(12) United States Patent
Vuong et al.

(10) Patent No.: US 7,270,784 B2
(45) Date of Patent: Sep. 18, 2007

(54) AUTOMATED LABORATORY FOR HIGH-THROUGHPUT BIOLOGICAL ASSAYS AND RNA INTERFERENCE

(75) Inventors: Minh Vuong, San Diego, CA (US); Todd Bennett, San Diego, CA (US); Javier Flores, San Diego, CA (US); Brian Grot, San Diego, CA (US); Daniel Hale, Carlsbad, CA (US); Huy Nguyen, San Diego, CA (US); Walter D. Niles, La Jolla, CA (US); Tuong Phan, San Diego, CA (US); Steve Rodems, San Diego, CA (US); Jeff Stack, San Diego, CA (US); Peter J. Coassin, Encinitas, CA (US)

(73) Assignee: Aurora Discovery, Incorporated, San Diego, CA (US)

( * ) Notice: Subject to any disclaimer, the term of this patent is extended or adjusted under 35 U.S.C. 154(b) by 0 days.

(21) Appl. No.: 10/837,218

(22) Filed: Apr. 30, 2004

(65) Prior Publication Data

US 2005/0054083 A1    Mar. 10, 2005

Related U.S. Application Data

(60) Provisional application No. 60/467,061, filed on Apr. 30, 2003.

(51) Int. Cl.
*G01N 21/00* (2006.01)
*G05B 15/00* (2006.01)

(52) U.S. Cl. .............................. 422/63; 50/65; 50/105; 50/67

(58) Field of Classification Search ........... 422/50, 422/63, 65, 99, 67, 105; 436/43, 45, 47, 436/48
See application file for complete search history.

(56) References Cited

U.S. PATENT DOCUMENTS

| | | | |
|---|---|---|---|
| 5,985,214 A | * | 11/1999 | Stylli et al. ............... 422/65 |
| 6,573,088 B2 | * | 6/2003 | Gemmell et al. ........ 435/286.4 |
| 2002/0009391 A1 | * | 1/2002 | Marquiss et al. ............ 422/63 |

* cited by examiner

Primary Examiner—Brian R. Gordon
(74) Attorney, Agent, or Firm—DLA Piper US LLP

(57) ABSTRACT

The invention is an automated multiple-purpose, integrated laboratory system comprising interchangeable modular elements for the construction and measurement of biological assays. The functions of the modular elements may include multiwell platform handling, chemical reagent or cell management, volumetric transfer of liquids for assay construction or for recovery of reaction products for analysis, incubation under controlled environmental conditions, measurement of spectrometric signals originating from the assays, processing and analysis of the resulting spectrometric data, and other functions. The modular elements are arranged around a number of robotic elements that deliver plates to different modular elements, transfer plates to groups of modules served by a different robotic element, or other actions necessary in plate handling. Liquid transfer to and from multiwell platforms, necessary for assay construction or for the initiation of physiological events in cells, is partitioned among different modules specialized for transferring nanoliter or smaller volume quantities of chemical concentrates, or microliter quantities of assay reagents, cells, media and other assay constituents. Applications of this invention include the quantitation and analysis of the expression of multiple genes in cells, measurement of multi-gene expression kinetics, analysis of activation or suppression of multiple signal transduction pathways, screening chemical compounds for modulatory effects on multi-gene expression or on signal transduction pathways or on other biochemical networks of cells, or other analytical biological or biochemical assays.

39 Claims, 6 Drawing Sheets

FIG. 5a

| Reagent | Condition | | | | | | | | |
|---|---|---|---|---|---|---|---|---|---|
| | 1 | 2 | 3 | 4 | 5 | 6 | 7 | 8 | 9 |
| | Instr. Blank | Exo. siRNA | Exo. siRNA | Nonspec. siRNA | Nonspec. siRNA | No. siRNA | No. siRNA | siRNA | siRNA |
| | unstim. | unstim. | stim. | unstim. | stim. | unstim. | stim. | unstim. | stim. |
| siRNA | - | + | + | - | - | - | - | + | + |
| Transfection reagent | - | - | - | + | + | + | + | + | + |
| scrambled siRNA | - | - | - | + | + | - | - | - | - |
| Biosensor Jurkat Cells | + | + | + | + | + | + | + | + | + |
| RPMI Growth medium | + | + | + | + | + | + | + | + | + |
| CCF2 signal development mix | - | + | + | + | + | - | + | + | + |
| Carbachol | - | - | + | - | + | - | + | - | + |

FIG. 5b

| 1 | 2 | 3 | 4 | 5 | 6 |
|---|---|---|---|---|---|
| 3 | 2 | 1 | 9 | 8 | 7 |
| 5 | 8 | 4 | 6 | 7 | 4 |
| 1 | 9 | 7 | 3 | 1 | 5 |
| 6 | 2 | 6 | 8 | 2 | 9 |
| 7 | 4 | 5 | 9 | 3 | 8 |

AUTOMATED LABORATORY FOR HIGH-THROUGHPUT BIOLOGICAL ASSAYS AND RNA INTERFERENCE

RELATED APPLICATION DATA

This application claims the benefit of U.S. Provisional Application No. 60/467,061, filed Apr. 30, 2003, titled, SCREENING DEVICES, the contents of which are incorporated by reference in their entirety.

BACKGROUND OF THE INVENTION

The invention relates to automated and integrated instrumentation and methods useful for the performance of analytical biological assays and reactions, particularly automated screening of low volume samples for new medicines, agrochemicals, cosmetics, and foodstuffs in assays in which multiple effects are simultaneously monitored on gene expression, signal pathway transduction, metabolic networks, and other complex biological systems.

Screening is an important early step in the drug discovery process. Modern biological research requires many diverse assays for specific biological activities in cells or isolated biochemicals in order to discover new biological targets for disease, new medicines directed to those targets, or other chemicals useful in the agrochemical, foodstuffs, cosmetics and other industries. An increasing number of assay types are being developed, including analyzing expression of particular genes, monitoring of activation or inhibition of signal transduction pathways, determining enzyme activity, measuring ion channel activity, quantifying levels of metabolites, and other analysis of biological activities and functions. As new assays become developed, they are put to use in discovering the molecular networks involved in normal physiological regulation of cells, control of gene expression, pathogenesis of various diseases, host physiological responses to pathogenic assault, and other knowledge useful in the diagnosis and treatment of disease. Drug development is beginning to require determination of the effects of combinations of chemical compounds on hundreds of genes and scores of signal transduction pathways to enable design of therapies tailored to the pathogenic mechanisms of a particular disease.

Biological assays often require extensive repetitively performed laboratory procedures to prepare a large number of samples that can then be run in parallel. In drug discovery, for example, a large number of identical assay samples are prepared, and then each sample receives a different, unique chemical compound to determine whether any of those compounds exert an effect on the biological activity probed by the assay that might merit pursuit as a therapeutic. Procedures used to construct these screening assays are generally typical of assay construction. Such procedures and tasks include handling a wide variety of liquids such as chemical reagents, cells, enzymes, substrates, cofactors, buffers, signal development reagent systems, or growth media in accurate and precise quantities. Assay construction is followed by accurate measurement of a signal, which is a change in a measurable physical output, that is produced by the assay and that indicates the time course or extent of the biological activity for which the assay was devised. The performance of assay construction and measurement is sometimes termed "staging".

Complexity of assay staging has lead to the development of automated laboratory systems including high-throughput assay systems (cf. U.S. Pat. Nos. 5,139,744; 5,985,214; 6,429,025; the contents of which are incorporated by reference in their entirety), which are automated and integrated instruments that handle the various aspects of assay staging. For example, to be efficient, chemical compound screens need to be conducted in a format that can maximize the information about chemical compound of potential interest with regard to a particular target while offering the ability to assess different targets to which the compound may exert its effect. This requires that each compound in libraries of millions of compounds be tested in a wide variety of assays, and each type of assay needs to be replicated as many times as needed to test all compounds.

Similar needs arise in molecular biological assays in which it is desired to understand gene expression. In gene expression analysis, messenger RNA is isolated from cells treated with a particular chemical compound, reverse transcribed to cDNA, amplified by the polymerase chain reaction (PCR) and then hybridized to single-stranded DNA segments encoding particular genes of interest to determine which gene's expression levels were altered by the chemical. Although these procedures can be routinely performed manually when less than 100 genes activities are assayed for each chemical tested, the number of genes of interest may run into the tens of thousands, and the number of chemicals that may exert desired but as yet unknown effects on their expression may number in the billions. The need for automation and increased throughput has lead to the development of automated thermal PCR cyclers and nucleic acid microarrays. In microarrays, robotic liquid dispensers are used to place nanoliter-volume liquid solutions of DNA segments, which encode genes, on glass or plastic substrates as small pads with length dimensions on the order of tens of microns. In an alternate method to liquid spotting, small, 20-nucleotide fragments of the genes are synthesized photolithographically on the substrate. Therefore, instrumentation systems that stage different biological assays and increase the throughput of each assay in a single organized system of work stations will benefit the performance of modern biological research and development.

Storage and assay plates traditionally have 96 or 384 wells. Over a thousand 96-well plates are needed to store 100,000 compounds and equally as many are needed each time a screen is run. A thousand plates can be cumbersome; handling them requires a room- sized automated storage-and-retrieval system. Also, since each well in the 96-well plate must be filled with about 200 microliters of reagent, the system needs to have a supply of about 20 liters to run a screen of 100,000 compounds. Screening in 96-well plates is quite a large operation.

Large, complex automation systems like those required to screen low-density plates must be located in a centralized facility. Only experts can operate the equipment, so companies that do screening usually have a dedicated screening team. An assay is transferred from the scientist who develops it to the screening team where it may sit in a queue for months. Running the screen may also take months depending on the number of compounds and the complexity of the assay.

To meet the increased demands and needs for assay performance, considerable attention has been devoted to decreasing the sample volume of assays while improving the ability of assays to discriminate small changes in biological activity, a process termed "miniaturization". Miniaturization efforts have been advanced with the intention of devising automated and integrated workstations capable of constructing and measuring numerous assays in parallel to achieve high throughput of experimental results. For example, the microtiter plate or multiwell platform has evolved from an industry-standard format of 96 wells, each containing a volume of ~200 μL, to increasingly higher densities of 384, 1536, 3456, and larger numbers of wells. This was achieved by subdividing the 8×12 well standard format of the 96-well plate to enable the use of sample volumes of less than 50, 10, and 5 μL to accommodate the demands of assay miniaturization to down to and the need to achieve high throughput handling of assays in parallel. About thirty 3456-well microplates are enough to screen 100,000 compounds, and required reagent volume drops by a factor of 100 compared to a 96-well plate. Principles and implementation of assay plate well miniaturization for high-throughput screening are disclosed in U.S. Pat. No. 6,232,114, the contents of which are incorporated by reference in their entirety. These platforms are now mass-produced standards in the industry, and available from numerous suppliers including Greiner, Coming, Nunc, and others. Multiwell microtiter plates provide a basis for much of the automated assay staging in high-throughput screening.

Miniaturization and parallelization efforts have also lead to the development of liquid handling and spectrometric measurement instrumentation specially suited to automated high-throughput biology. Automated liquid handling is required to achieve the throughput requirements in miniaturized assays because the manually operated piston-plunger dispensers used for pipetting volumes >10 μL become cumbersome, inaccurate, and imprecise when repetitively transferring smaller volumes. Miniaturization of automated liquid handling has encompassed handling at least two ranges of volumes needed for miniaturized assays. The first range is from 1 microliter to 10 nanoliters, which encompasses the volume increments needed to construct assays from a variety of constituents comprising cells, media, assay signal development reagents, enzymes or other assay reagents, in which the total volume per well is less than 5 μL. A widely used technology is the solenoid-actuated valve, in which the liquid to be dispensed is maintained at a constant hydrostatic pressure behind the valve, and the valve solenoid is actuated for a few milliseconds to dispense the liquid through an outlet with an orifice diameter of about 100 μm. To dispense the same liquid to multiple miniaturized wells in an assay platform simultaneously, multiple dispensers are aligned with their orifices spaced according to the well pitch using a fixturing mechanism such as a multi-orifice plate. The target multiwell plate is automatically repositioned under the orifice or multiple orifice fixture at locations that are integral multiples of the center-to-center spacing of the wells to fill the wells of the plate. This type of positioning achieves accuracy and reliability because the different tubes and lines that feed the dispenser are not subject to movement and compression and, hence, ejection pressure variance. Dispensing systems of this type are disclosed in U.S. Pat. No. 5,985,214, the contents of which are incorporated by reference in their entirety. Nonetheless, in some systems, the dispenser head is moved over a stationary receptacle. This type of dispenser is available commercially from several vendors, such as Genomic Solutions, Biodot, and others, in different configurations adaptable to the dimensions of the platform in which the assays are constructed.

The second range of volumes needed in miniaturized assays extends below 10 nL. The requirement for this volume range arises in assays where relatively small volumes of a chemical compound concentrate are added to an assay during construction. The need for the small relative volume arises because the compound may be dissolved in a non-aqueous solvent, such as dimethylsulfoxide or benzene, which may exert its own effect in a biological assay. The objective is to dilute the small volume of solvent (e.g., 1 nL) with the relatively much larger volume of aqueous assay diluent (1 μL) to a concentration where biological effects are mitigated. This situation arises in the screening of chemical compound libraries for new therapeutics. To obtain these low volumes, ink-jetting technologies such as thermal- or piezo-actuation have been adapted to biological assay construction. A commercially available piezo-actuated dispenser for miniaturized assay construction is the Microdrop from PE Biosystems. A new technique for small-volume dispensing is surface acoustic wave control in which the surface of the liquid to be dispensed is energized to produce a standing stationary wave. Energization is provided by a small acoustic lens, such as a curved piezoelectric ceramic lens brought into contact with the bottom of the container of the liquid. Dispensing of pico- or nano-liter sized drops is actuated by the addition of a high-amplitude transient pulse to the energizing wave, which causes reorganization standing wave modes into a jet that projects from the liquid surface and coalesces into a drop the volume of which depends on the amplitude of the actuation pulse. This technique is disclosed in U.S. Pat. No. 4,751,530, the contents of which are incorporated by reference in their entirety, and is available as a commercial system from EDC Biosciences as the HTS-01. Thus, a variety of technologies for liquid handling are presently available for integration into high-throughput biological screening systems.

Rapid detection and measurement of the signals developed in miniaturized biological assays has required several innovations. One advance has been the invention of multi-well assay platforms with clear well bottoms having high transmittance to the wavelengths of light generated by the biological assay. In addition, plastic, injection-moldable materials have been developed to provide a composition for both the clear well bottoms and black well sidewalls materials with greatly decreased intrinsic fluorescence (autofluorescence) at the wavelengths of light used to excite the fluorescent assay signal development systems used to detect and measure biological activity. These advances in plate technology greatly decrease both the background fluorescence originating from the plate materials as well as extraneous fluorescence originating from assays in neighboring well of the platform and allow the small fluorescence signals developed by a small number of cells in a single well to be accurately measured. These inventions are disclosed in U.S. Pat. No. 6,517,781, the contents of which are incorporated by reference in their entirety.

Miniaturized optical assemblies or heads enable spectrometric signals to be accurately and precisely measured in miniaturized assay wells as disclosed in U.S. Pat. No. 5,985,214, the contents of which are incorporated by reference in their entirety. The clear bottom of a single well may provide a window diameter of only 0.9 mm or less, and the assay signal may originate from as few as 300 fluorophores in only 10 to 20 cells in the well. Thus, these optical heads need to be accurately positioned to within only a few tenths of a millimeter away from the well bottom in order to enable injecting the excitation light into the assay well being measured without appreciable introduction of excitation light into adjacent wells. In addition, the heads need to provide sufficient numerical aperture to enable capture enough of the resulting light emitted by the assay in the well to allow an appreciable signal to be measured that is proportional to the biological activity being probed in the assay. This has lead to the development of optical heads using a ball lens that is positioned close to the well bottom and that is interposed between the clear well bottom and the face of a bundle of optical fibers. This fiber bundle is subdivided into two or more sub-bundles so that one sub-bundle conveys the light of the excitation wavelengths from a source, such as an arc lamp, through an interference filter or other means to isolate the excitation wavelengths of light to the ball lens for illumination of the well contents through the clear bottom. The ball lens captures a portion of the light emitted by the signal development system of the assay in the well through the clear well bottom and focuses this light onto the face of the optical fiber bundle. The remaining sub-bundles transmit this light away from the ball lens. At the opposite end of each sub-bundle is an interference filter that passes only the wavelengths of emitted light that are to be measured in the assay to the face of a photosensitive detector such as a photodiode, photomultiplier tube or charge-coupled device. The multiplicity of sub-bundles enables multiple emission wavelengths to be measured from multiple fluorophores in the assay, such as donor and acceptor emission intensities of resonance energy transfer probes, or different fluorophores in the same cell that report the activities of different biological molecules.

To read the assay samples in the different wells of a multiwell plate, the optical head is brought up to its action position under the clear bottom of each well. For stability reasons, this is typically achieved by repositioning the plate over a fixed optical head by the use of automated X-Y positioners. Because the plate bottom may not be sufficiently flat to within the ~100 μm spacing requirements of the optical head with respect to the well bottom to achieve a constant numerical aperture for reading of each well, topographical corrections have been implemented. The vertical position of the center of each well bottom is measured, such as by a laser displacement sensor, and then the vertical location of each well is used to position the plate vertically over the optical head to obtain the same numerical aperture for every well. Since modern photodetectors can be operated in single-photon detection mode, only a very brief dwell time of the well over the optical head is needed to obtain a spectrometric reading. This enables, for example, a multiwell plate consisting of an array of 48×72 wells (3456 wells total) to be read in as little as 2 min. Thus, spectrometric readers are available that are capable of handling the throughput and sensitivity demands posed by running a large number of miniaturized biological assays in parallel.

As the components needed to perform the various tasks of assay construction and measurement have been developed, integration of these devices into automated systems has become the key to enabling high-throughput biological assays. One of the earliest efforts at an automated laboratory workstation is the Biomek (Beckman Instruments, Fullerton, Calif.) as disclosed in U.S. Pat. No. 5,139,744, the contents of which are incorporated by reference in their entirety. In the Biomek, multiwell plates are located at different areas on a work surface that are functionally defined so as to identify each plate as being either a source of an assay reagent material or a destination for the mixing of an assay. The functionally defined locations provide the sets of coordinates needed by the controller for a robotic arm to position the arm at specific locations over each plate. An array of micropipettes connected to a positive-displacement pump was fixed at the end of the robotic arm. By using the plate positions coded by the functionally defined work surface, the controller could position the micropipettes in the wells of the source plates, aspirate the chemical reagent samples needed, raise the arm, position the pipettes in the wells of the destination plates, and dispense the reagents to the assay under construction. Assay construction could be programmed so as to aspirate and dispense liquid volumes selected by a user from a variety of source and destination plates. The Biomek automated the many repetitive volumetric liquid transfer tasks involved in assay construction and could be adapted to a wide variety of solution-based assays. More extensive assay task control and integration of several laboratory work stations performing different assay tasks is embodied in the system for automated drug discovery screening of chemical compound libraries disclosed in U.S. Pat. No. 5,985,214, the contents of which are incorporated by reference in their entirety. In their ultra-high throughput screening system, a robotic arm was used to place multiwell plates containing compounds from the compound library onto a set of parallel conveyer lanes, which queued the plates into plate stackers that provided plates to different liquid handling and assay measurement modules located at spur transports, perpendicular to the main transport lanes. For example, one liquid handler aspirated the chemicals from the compound library plate, transferred each chemical to a separate well in a fresh plate, and then added a diluent to each well to provide the dilution of chemical in the assay buffer necessary for performance of the assay. These dilution plates were then maintained in a plate stacker and delivered one at a time to a transport lane where they were conveyed to a different workstation where the diluted chemicals were transferred to plates in which the assays were constructed.

Despite its advantages, miniaturization is still not feasible for most companies. One hurdle is that new instrumentation is required to access the small wells of high-density microplates because the dispensers and plate readers designed for low-density plates will not work with 1536- or 3456-well microplates. Anther issues is that most of the instruments available today cannot transfer liquid from one high-density plate to another. This means that compounds must still be stored in thousands of low-density plates inside a room-sized machine. Even if screening is being done in high-density microplates, the advantages of miniaturization are only half realized.

SUMMARY OF THE INVENTION

The invention is an automated multiple-purpose, integrated laboratory system comprising different modular elements for the construction and measurement of biological assays. The modular elements accommodate microtiter plates having a large number of microliter-volume sample wells in a standard high-density, miniaturized format for storage of chemical compounds, for construction and performance of numerous biological and biochemical assays in parallel, and for other purposes. The modular elements serve a function in performance of biological assays. These diverse functions include multiwell platform handling, chemical reagent or cell management, volumetric transfer of liquids for assay construction or for recovery of reaction products for analysis, incubation under controlled environmental conditions, measurement of spectrometric signals originating from the assays, processing and analysis of the resulting spectrometric data, and other functions. The modular. elements are arranged around a number of robotic elements that deliver plates to the different modular elements, transfer plates to groups of modules served by a different robotic element, or other actions necessary in plate handling. Liquid transfer to and from multiwell platforms, necessary for assay construction or for the initiation of physiological events in cells, is partitioned among different modules specialized for transferring nanoliter or smaller volume quantities of chemical concentrates, or microliter quantities of assay reagents, cells, media and other assay constituents. Acoustic energy is employed for dispensing and reagent mixing, for sensing the volume of liquid in each well of a plate, for stopping an assay or reaction by ultrasonic disruption, or other functions. Other modules perform spectrometric or other measurements on each well using adaptive positioning of optical or other detection elements under each well of a platform to enable precise illumination and collection and separation of multispectral signals originating from an assay. Modules are interchangeable at different stations along the path served by a robotic arm to enable, for example, recovery of polymerase chain reaction products for sequencing by capillary electrophoresis, analysis of expressed proteins and their glycosylation sequences by mass spectrometry, or other analytical procedures and techniques. Assays are constructed and measured using a user-configured interactive controller that programs the delivery of multiwell plates to the different modules and specifies the needed parameters for each module to act upon each well of a plate. Applications of this invention include the quantitation and analysis of the expression of multiple genes in cells, measurement of multi-gene expression kinetics, analysis of activation or suppression of multiple signal transduction pathways, screening chemical compounds for modulatory effects on multi-gene expression or on signal transduction pathways or on other biochemical networks of cells, or other analytical biological or biochemical assays.

The present invention provides key functions and enhancements that enable the automated laboratory access to a wide variety of assays and analytical procedures that were not capable of being implemented in earlier systems. For one, plate handling is integrated and self-contained in a smaller working space such that a single pair of transport lanes are required. The modules needed for the construction and measurement of assays are capable of being removed from the stations along the transport path and replaced with modules of different functionality. For example, the standard spectrometric module typically used to measure assay signals of a fluorescence or absorbance nature can be replaced with a miniaturized mass-spectrometric module to enable analysis of changes in peptide, carbohydrate, lipid, or other biomolecular constituents of cells in response to the action of an exogenous chemical on cellular function. This extensible modularity enables a wider variety of assay tasks to be performed and a much wider variety of assays to be constructed and measured by the use of a single, self-contained system.

The following references are, in addition to that which is described as background, the invention summary, brief description of the drawings and the abstract, hereby incorporated by reference into the detailed description of the preferred embodiments below, as disclosing alternative embodiments of elements or features of the preferred embodiments not otherwise set forth in detail below. A single one or a combination of two or more of these references may be consulted to obtain a variation of the preferred embodiments described in the detailed description herein:

Astle, T. 1996. Standards in robotics and instrumentation. Journal of Biological Screening. 1 (4):163-169.

Bohm, S., N. Chiem, J. Gilbert, J. Lapidas, A. van den Berg,. and T. Veenstra. In Vitro Diagnostic Technology, July/August, 2003, 37-45.

Buote, W. J. 1988. Computerized robot control system with scheduling feature. U.S. Pat. No. 4,727,494.

Chan, E. Y. 2001. Molecular motors. U.S. Pat. No. 6,210,896.

Chan, E. Y. 2002. Methods of analyzing polymers by ordered labeling strategies. U.S. Pat. No. 6,403,311.

Coassin, P. J., A. T. Harootunian, A. A. Pham, and R. Y. Tsien. 2001. Low background multi-well plates for fluorescence measurements of biological and biochemical samples. U.S. Pat. No. 6,232,114.

Coassin, P. J., A. T. Harootunian, A. A. Pham, H. Stylli, and R. Y. Tsien. 2003. Low fluorescence assay platforms and related methods for drug discovery. U.S. Pat. No. 6,517,781.

Dannoux, T. L. A. 2002. Method of making an extruded high density assay plate. U.S. Pat. No. 6,463,647.

Ebashir, S. M., W. Lendeckel, and T. Tushci. 2001. "RNA interference is mediated by 21- and 22-nucleotide RNAs." Genes and Development. 15:188-200.

Elrod, S. A., B. T. Khuri-Yakub, C. F Quate. 1988. Acoustic lens arrays for ink printing. U.S. Pat. No. 4,751,530.

Hutchins, B. M., T. B. Fowler, D. Friswell, P. A. Kearsley, B. A. Swanson, E. T. Tetrehault, and J. Elands. 2000. Robotic system for processing chemical products. U.S. Pat. No. 6,068,393.

Kowalski, C. 1992. Automated laboratory work station having module identification means. U.S. Pat. No. 5,139,744.

Makings, L. and G. Zlokarnik, 2003. Optical molecular sensors for cytochrome P450 activity. U.S. Pat. No. 6,514,687.

McManus, M. T. and P. A. Sharp. 2002. "Gene silencing in mammals by small interfering RNAs." Nature Reviews Genetics. 3:737-747.

Parce, J. W., A. Kopf-Sill, and L. J. Bousse. 2002. High-throughput screening assay systems in microscale fluidic devices. U.S. Pat. No. 6,429,025.

Schena, M. 2003. Microarray Analysis. John Wiley and Sons, New York. 293 pp.

Stylli, C., S. S. Beckey, C. B. Schumate, and P. J. Coassin. 1999. Systems and methods for rapidly identifying useful chemicals in liquid samples. U.S. Pat. No. 5,985,214.

Vuong, T. M. 2003. Multiwell scanner and scanning method. U.S. Pat. No. 6,586,257.

Williams, R.; Singh, T.; Mansour, N.; Lee, Jr., L; and Forbush, M. 2003. Acoustically mediated fluid transfer methods and uses thereof. U.S. Pat. No. 6,596,239

BRIEF DESCRIPTION OF THE DRAWINGS

The drawings accompanying and forming part of this specification are included to depict certain aspects of the invention. A clearer conception of the invention, and of the components and operation of systems provided with the invention, will become more readily apparent by referring to the exemplary, and therefore nonlimiting, embodiments illustrated in the drawings, wherein identical reference numerals designate the same components. The invention may be better understood by reference to one or more of these drawings in combination with the description presented herein. It should be noted that the features illustrated in the drawings are not necessarily drawn to scale.

FIGS. 5a-5b show a dispensing table for a siRNA knockdown experiment and well map.

DESCRIPTION OF PREFERRED EMBODIMENTS

The invention and the various features and advantageous details thereof are explained more fully with reference to the nonlimiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating preferred embodiments of the invention, are given by way of illustration only and not by way of limitation. Various substitutions, modifications, additions and/or rearrangements within the spirit and/or scope of the underlying inventive concept will become apparent to those skilled in the art from this disclosure.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of the "a" or "an" are employed to describe elements and components of the invention. This is done merely for convenience and to give a general sense of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Figure 1A:
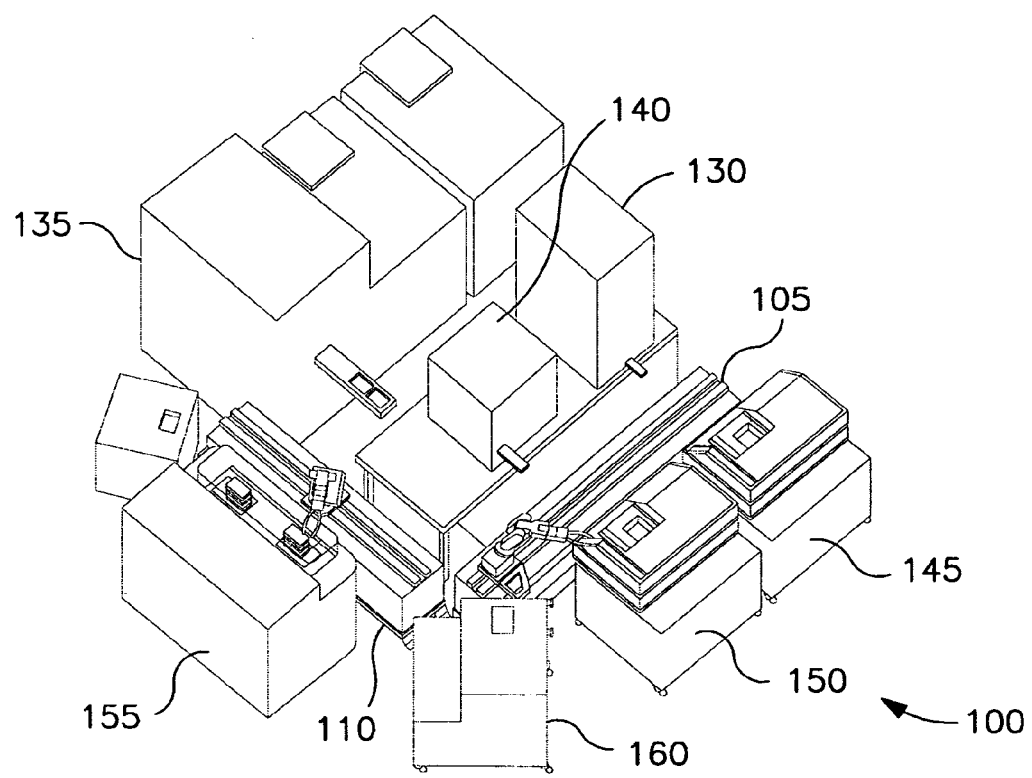
FIG. 1a shows a perspective view of one embodiment of an automated high-throughput biology laboratory.

The invention is directed to an automated multiple-purpose, integrated laboratory island or automated high-throughput biology laboratory comprising different modular elements. FIGS. 1a and b show embodiments of the automated high-throughput biology laboratory 100 that enables screening and compound storage in high-density microplates. The biology laboratory 100 may consists of one or more of the following components or modules used in combination; plate readers, microliter dispensers, nanoliter dispensers, incubators, plate carousels, robots, a centrifuge, and a computer system with control software connect to the various components or modules.

Each module provides a needed function in the performance of biological assays. These functions include multiwell platform transport between units used to store or incubate platforms and the individual functional modules as well as platform positioning to a high degree of spatial accuracy within each module. Additional functions include coordinated management of the chemical reagents or compounds or cells such that the different components of each assay are delivered to the assay samples at the needed times and in the proper order. Other functions include quantitative handling of liquids by various means to transfer liquids to sample wells in the platforms for assay construction or to recover reaction products resulting from the biological activity of cells in sample wells for analysis. Still other functions are the incubation of assays under controlled environmental conditions, measurement of spectrometric signals originating from the assays, processing and analysis of the resulting spectrometric data, and other functions. These functions are provided by exchangeable instrumentation units or modules that can be added at stations along the biology laboratory island to provide the needed functionality or removed to provide an available station for the insertion of another module providing a different functionality. In one embodiment, the operations of these modules are integrated such that a single computer program providing an integrated interface to the user controls them. Through this interface, assay operation parameters such as which plates contain particular reagents needed for construction of an assay, where these plates are to be transferred, the volume of reagent to be transferred to or from the plate, measurements to be obtained from a plate, or other quantities or conditions needed for the successful construction or reading of an assay or reaction are provided to the different modules. This integration of control enables all the elements of staging an assay to be directed from a single central location. The program references the driving code for each module on insertion into the island so as to provide "plug and play" functionality.

Each module accommodates multiwell platforms that are manufactured in accordance with industry standards for robotic automation and miniaturization of biological assays and that have a large number (>1500) of wells with transparent bottoms in a high-density format. These plates are used for storage of small (<10 µL) volumes of chemical compounds, for construction and simultaneous performance of numerous biological and biochemical assays in parallel, or for other purposes. The modular elements are arranged around multi-lane conveyer tracks to enable conveyance of plates to and from the different modules. These plate handlers comprise a number of robotic arms each mounted on a track, and thus capable of manipulating these plates in actions such as placing or removing lids, delivering plates to different modules, and transferring plates to different conveyers with modular elements served by a different robotic arm.

One feature of the automated high-throughput biology laboratory 100 is the incorporation of multiple modalities for volumetric liquid transfer in order to encompass a wide range of liquid volumes needed for the performance of miniaturized biological assays. These different modalities are incorporated into different modules each specialized to handle the quantitative transfer of a particular range of volumes. Volumes in the microliter to tenths-of-microliter range are transferred to assay samples using hydrostatic pressure actuated by electronically controlled microvalves, whereas volumes in the tens-of-nanoliters to picoliter range are dispensed by acoustic driving. Removal of assay samples from wells utilizes microcapillary sippers to convey the contents of wells to microcapillaries that can then be used to introduce the samples into other analytical instrumentation.

Another feature of the automated high-throughput biology laboratory 100 is the incorporation of acoustic means for the performance of diverse tasks needed in assay construction and measurement. Surface acoustic wave control is used to dispense small, nanoliter-scale quantities of liquids and to control their placement into assay sample well. Acoustic energy is also used in a variety of other functions, such as detection of the heights of liquids in well. Ultrasound is used to promote the dissolution of chemical compounds or other molecules in liquids for which the solubility is low. Ultrasound is also utilized as a biological fixation means, in which disruption of the cells in a sample well not only stops the biological reactions underway but also disperses the cellular contents throughout the assay well for removal and further separation, extraction, or analysis.

Still another feature of the automated high-throughput biology laboratory 100 is the ability to accommodate a variety of modules for accurate measurement of signals arising in assays. These include modules for spectrometric measurements such as absorbance or fluorescence readers as well as mass spectrometers or other integrated modules providing extensive capabilities such as nucleic acid sequencing. A primary capability of these modules is the ability to isolate the assay signals arising in each sample well by precise adaptive positioning of optical elements under each well of the plate. In the case of fluorescence measurements, this allows the contents of each well to be illuminated and the resulting multispectral emissions to be measured without interference by possible fluorescence signals in adjacent wells. The modularity of measurement enables a wide variety of spectrometric assays to be performed, since a module whose function is specialized for a particular measurement can be substituted for another module at a measurement station.

Still another feature of the automated high-throughput biology laboratory 100 is the ability to interchange measurement and liquid transfer modules at different stations along the path served by a robotic arm to enable the performance of a wide variety of relatively complex assays. For example, a capillary sipper can be paired with a multiplexed array of dispenser needles served by a positive displacement pump. This enables the acoustically disrupted contents of the wells of a microtiter plate to be transferred to a specialized, non-industry format substrate matrix. The matrix can then be transferred to a matrix-assisted laser desorption ionization time-of-flight (MALDI-TOF) mass spectrometer for parallel analysis of expressed proteins, their glycosylation sequences, or other biological molecules of interest. An alternate use of the capillary sipper could be recovery of the products of polymerase chain reactions conducted in a microtiter plate for sequencing by capillary electrophoresis, or other microanalytical procedures and techniques. Applications of this invention include the quantitation and analysis of the expression of multiple genes in cells, measurement of multi-gene expression kinetics, analysis of activation or suppression of multiple signal transduction pathways, screening chemical compounds for modulation of the expression of multiple genes or of signal transduction pathways, and other analytical biological or biochemical assays.

Basic layout: The automated high-throughput biology laboratory 100 is arranged as a self-contained set of components or modules in which the different modules are located around a multiwell platform handling system. The layouts described provide examples of systems designed for a wide variety of assays but more general systems can be designed as well more specific arrangements suited to particular instances. The essential features is that each module contains a platform access port which allows for the insertion into and retrieval of plates and this port is located where it can be accessed by a robotic device that loads and unloads the plates from the conveyance used by the module to handle the plates.

Figure 1B:
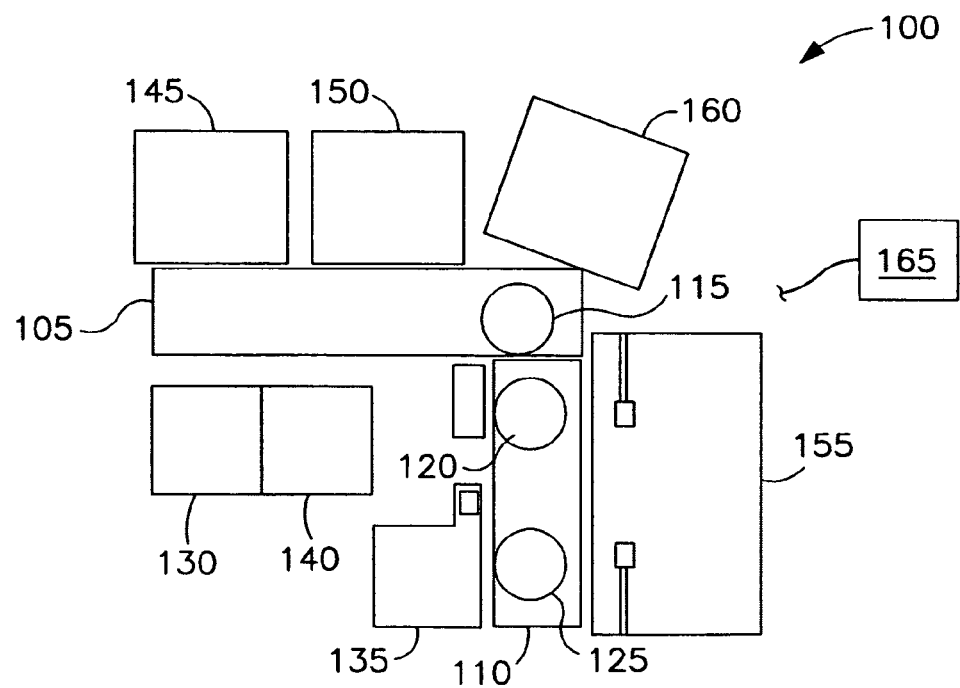
FIG. 1b shows a plan view of one embodiment of an automated high-throughput biology laboratory.

FIG. 1a shows a perspective view of one embodiment for automated high-throughput biology laboratory and FIG. 1b shows a plan view. The modules that perform the different assay tasks in construction or measurement are deployed around two linear plate transports 105 and 110. These transports may be of the type described in U.S. Pat. No. 5,985,214, which are equipped with devices to lift and transfer plates to plate conveyers located in each module. In one embodiment, each transport consists of a plate gripper located at the end of an articulated robotic arm that is mounted to a rotary stage located on a linear translation stage, such as the CataLyst-5 track system (Thermo CRS) or other robotic arms mounted on a track. To transfer a plate between modules, the arm extends to place the gripper around a plate presented by a source module on a special caddy designed to accept the components of the gripper that contact the plate. The gripper is actuated to grip and the arm lifts the gripped plate from the caddy and retracts. The arm is translocated along the linear track to new service location where the plate caddy from the destination module is extended to receive the plate from the arm. The arm extends to place the plate in the caddy, the gripper is actuated to release the plate, and the transfer is complete. Multiple arms may be located on a track. Example service locations of the arm located on each track 105 and 110 are depicted at locations 115, 120, and 125.

Plate and reagent storage is accommodated in the basic layout with plate carousels 130 and 135, and incubators 140. The carousels 130 and 135 serve to maintain a supply of empty plates, plates filled with chemical reagents, buffers, diluents, compounds or other liquid chemicals used to construct assays, or plates containing either partially or completely constructed assays that do not require special environmental conditions. In one embodiment, a library of compound microplates is stored in one plate storage carousel 130 and a library of assay microplates is stored in another plate storage carousel 135. Incubators 140 may contain empty plates, plates filled with chemical reagents, buffers, diluents, compounds or other liquid chemicals used to construct assays, plates containing cells in culture, medium, or plates containing either partially or completely constructed assays that are required to be maintained at specific conditions of temperature, darkness, humidity, atmospheric composition, or other conditions. The incubators 140 may also be used as repositories for constructed assays that have been started and require a period of time (e.g., >20 min) for generation of the assay signal.

Dispensing of liquids in the system 100 uses one or more dispenser modules 145, 150, and 155. In one embodiment, dispenser modules 145 and 150 contain pressure-driven solenoid-actuated dispensers as described in "Handling different ranges of liquid volumes" or larger format dispenser arrays as described in U.S. Pat. No. 5,985,214, while dispenser module 155 may be an acoustic-controlled dispenser such as the EDC Biosystems HTS 01. In some embodiments, dispenser modules 145 and 150 may be microliter dispensers that can dispense reagent volumes as low as 100 nL and dispensing module 155 may be a nanoliter dispenser that uses a focused acoustic radiation pressure beam that ejects droplets of compound as small as 1 nL directly from a storage plate into an assay plate.

In the embodiment shown, the rationale for siting two dispenser modules 145 and 150 of the same type on one track 105 with a different dispenser module 155 on the second track 110 is that the different source and destination platforms may be used for the two types of dispenser systems and one type of dispenser may be used at different stages of assay construction. For example, in chemical compound screening assays, subnanoliter volumes of concentrates of chemical compounds in non-aqueous solvents such as dimethylsulfoxide may be the first component added to the platform used to build the assay typically using a dispenser of the type located at 155. This type of dispensing requires a smaller volume range than is typically needed for delivery of the other reagents and cells needed for the assay, and, hence, is readily handled by a different dispenser. In this case, the compounds are dispensed from a source plate initially maintained in a carousel and delivered to a plate handling port. The compounds are delivered to a destination plate by the dispenser and this plate is then returned to a carousel or incubator to allow the solvent to evaporate or the compound to distribute on the well bottom.

By contrast, addition of aqueous materials to an assay may require several sequential additions of different materials, such as cells, medium or medium substitute, chemical reagents needed to enable the assay to progress or signal development systems, or other chemical reagents such as agents needed to facilitate entry of the signal development reagents into cells or to cause the cells to activate the signal development reagents. These additions may be performed with the same type of dispenser but may be limited by the capacity of a single dispenser module. Therefore, two dispenser modules 145 and 150 of the same type located along the same track 105 enables the rest of the chemical screening assay to be constructed rapidly from separate components without limitations imposed by the capacity of one module. In a chemical compound screening assay, the destination plate containing the already dispensed compounds might visit one dispenser module, for example dispenser module 145, to be loaded with cells and signal development reagents, and then visit the second dispenser module, for example dispenser module 150, to receive the activator or modulator of the assay to start the biochemical reactions monitored by the assay.

The dispensing methodologies used in some embodiments of the invention are non-contact. Dispensing to the destination wells of the high-density multiwell plates does not require the capillary action obtained when a probe or pin containing the liquid to be dispensed contacts the destination surface. This avoids the inherent inaccuracies of contact dispensing, such as inadvertent wetting of the side of the probe or pin with sample that results in partial delivery to the destination. This also avoids both contamination of the dispenser with material already present in a sample well and unwanted carryover between samples.

In some embodiments, there are situations where it is necessary to aspirate the sample in an assay well and distribute it for subsequent analysis. These situations might include the validation of a targeted knockout of the message of a particular gene to determine that the particular gene product was successfully knocked out or other desired analysis. These analysis might be performed by, for example, reverse transcription and polymerase chain reaction to convert the message of siRNA-treated cells to DNA sequences that could be probed by binding to beads linked with a single-stranded DNA sequence complementary to the cDNA expected to be produced had the siRNA not knocked out the transcript and then sequencing the resultant cDNA bound to the bead-linked probe. The resultant cDNA could instead be analyzed by traditional microarray analysis. The aspirated sample cells could also be lysed, the protein precipitated by ammonium persulfate, separated by electrophoresis, and immunoblotted to determine the absence of the desired knocked out gene product. In these cases, a modular station may be implemented in the present invention such as a Sciclone ALH (Caliper Life Sciences, Mountain View, Calif.). The Sciclone ALH is a robotic platform using more traditional plunger-driven positive displacement pumps connected to disposable pipette tip fixtures or microcapillaries that could be lowered into the miniaturized sample wells for aspiration and then subsequent transfer to the substrate used for analysis.

The assay signal detection module or plate reader 160 may be any of a number of instrument modules capable of reading the physical output of an assay. These modules may be adapted for detection and measurement of a wide variety of physical signals for which assays may be constructed and which provide indications of the biochemical or biophysical states of cells that are desired to be measured. In one embodiment, this module may be a spectrometric reader such as a fluorescence reader capable of visiting each well of a multiwell assay plate, illuminating its contents, and measuring the light intensities emitted by the assay sample in a number of wavebands. In one embodiment, changes in the fluorescence signal are determined as the ratio of fluorescence at two different emission wavelengths using means known in the art. In addition to the possible different spectrometric modalities including absorbance, fluorescence, resonance energy transfer, time-resolved fluorescence or resonance energy transfer, polarization fluorescence, or other mono- or multispectral luminescence or fluorescence modalities, this instrumentation may be readily adapted to use novel fluorophores, such as those developed for use with infra-red wavelengths of light, or Quantum dots, which are inorganic semiconductor materials that absorb light over a relatively uniform spectrum of wavelengths but emit in very narrow wavebands of light according to their particle size. In other embodiments, this module may a combined dispenser and fluorescence plate reader as described in "Kinetic assays". The only requirements for these detection modules are that:

1. Each module is capable of receiving from and presenting to the robotic arm the multiwell assay plates, and
2. Each module is equipped with internal mechanical translation mechanisms capable of positioning the multiwell assay plates in the vicinity of the active measurement element or elements of the detector such that the signals originating from each well can be measured and recorded.

These requirements are not prohibitive in the range and type of module that may be used for measurement. For example, plate entry and exit points and sample holders can be modified to accept a standard plate holder and set of translation stages needed to obtain the X- , Y-, and Z-motions needed to bring a plate to the active element and remove it after measurement. In addition, a standard plate holder and translation stage system can be customized to provide plate handling for modules of different sizes and form factors. Similarly, the requirement for access by the active element to all wells of a multiwell plate can be achieved by building the plate translation stages to position each well in the proper reading position with respect to the active element and then reading each well in sequence. The multi-axis translation stage and electronics associated with imaging and data collection can be managed by an appropriately programmed digital computer. The computer also can transform the data collected during the assay into another format for presentation. The time to read a 3456 well microplate is approximately 1 minute.

One of the advantages of the automated high-throughput biology laboratory 100 is the versatility and flexibility with which new measurement modules can be incorporated into the system. The choice of module depends on the needed functionalities. The following measurement capabilities are listed to provide examples of this diversity and flexibility.

1. In one embodiment, DNA sequencing can be performed by incorporating a high-throughput sequencing device such as the ABI 3700 (PE Biosystems). This sequencer uses glass microcapillaries with small outer diameters (~1 mm) to aspirate DNA samples prepared by the Sanger reaction and end-labeled with fluorophores from 96 or 384-well plates for capillary electrophoresis. The capillaries are arranged in a 2-dimensional planar comb compatible with the industry-standard center-to-center distances for these plates. These capillary combs can be adapted for use with higher-density plates by the use of linear translation stages with spatial positioning accuracies of <25 μm to center each capillary over a grid of wells. This position can then be indexed according to the pitch of the higher-density well plates so that these plates can be used, as well.

2. In another embodiment, DNA sequencing may also be performed using microfluidic systems such as the GeneEngine (US Genomics). The GeneEngine performs sequence analysis on single, linear fragments of DNA or RNA in which each base is tagged with a specific fluorophore. The linear strand of nucleic acid is captured by a laminar flow stream in a narrow microfluidic pathway and extended. The extended strand is passed through a fluorescence detection element that reads the identity of each base depending on the quantum distribution of emission as each base encounters the illumination. The GeneEngine allows the sequencing of nucleic acid without amplification, and so is suitable for detecting the presence of an altered gene in a cell, which may underlie an altered phenotypic response of the cell to a modulator or agent.

3. In another embodiment, separation of nucleic acids, such as in a sample of cells in a well subjected to a particular condition for which it is desired to be known whether changes in gene expression have occurred and then disrupted to release the cellular contents, can be performed using the AMS 90 SE (Caliper Technologies). This capillary electrophoresis device uses capillaries lowered into well containing sample liquids to aspirate the liquids into the active elements by capillary pressure. This "capillary sipper" innovation of great utility in transferring microliter volumes of liquid samples from high-density multiwell plates into the active elements of measurement modules, especially those that are miniaturized for measurements of small liquid volumes such as microfluidic platforms (Parce et al, 2002). Other capillary or acoustic means are also available for transferring samples from high-density multi-well plates to other miniaturized analytical substrates or platforms. A summary of these type of fluidic transfer by Bohm et al, 2003 describes a number techniques for integrating microfluidic platforms with automated laboratory equipment.

4. In another embodiment, separation and analysis of proteins, peptides, carbohydrates, small organic molecules such as metabolites, or other molecules of biological interest can be performed using a variety of technologies in common use that have been adapted for the use and handling of miniaturized samples. For example, gas chromatography of liquid samples may be performed with the 6890N gas chromatograph (Agilent Technologies), which is adapted to throughput of tandem samples by automated purging. Mass spectrometry, a routine method for molecular separation and analysis, may be performed using platforms from Thermo Finnigan, Mass Technologies, Kratos Analytical, or Brucker Daltonics. Mass Spectrometry adapted for the analysis of the total protein content of cells such as MALDI-TOF is available as the 4700 Proteomics Analyzer (PE Biosystems). Each of these platforms is adapted or adaptable to sample introduction from multiwell plates.

5. In another embodiment, novel and unique modes of detecting and measuring physiological events in cells such as multipole coupling spectroscopy (MCS) may be utilized with new types of detectors, such as microwave polarization spectrum analyzers (Signature Biosciences). MCS uses surface-polarized microwaves to measure changes in the dielectric structure of macromolecules such as those caused by binding a ligand or allosteric conformation changes. Samples used in MCS assays are deployed in wells fabricated as microfluidic features on special substrates needed for impedance-matched coupling to the measurement device. These miniaturized wells are amenable to the assay construction and performance systems incorporated in this invention, which extends the utility of this new assay methodology.

Thus, the automated high-throughput biology laboratory 100 provides a complete system for the performance of a wide variety of biological assays and is unlimited in its ability to extend its usefulness by incorporating new signal measurement technologies as they become available.

While the automated high-throughput biology laboratory 100 is susceptible to various modifications and different forms, specific embodiments thereof are shown by way of example in the drawings and the accompanying descriptions. It is not intended to limit the invention to the particular forms disclosed, but the invention is to cover all modifications, equivalents, and alternatives falling within the concept of the invention defined by the claims.

As discussed above, the automated high-throughput biology laboratory 100 is directed to laboratory systems that use automated and integratable workstation modules for the performance of biological assays. These assays may be directed to many different uses such as screening of chemical compounds to discover new medicines or other useful and desirable properties of chemicals, mapping enzyme networks in cells mapping control networks of gene expression, elucidating mechanisms of signal transduction and determining the cellular constituents comprising signal transduction pathways, determining mechanisms of pathogenesis, such as the control of gene expression in bacteria when stimulated to form a biofilm, the host response to an etiologic agent, or other pathogenic activity, determining other desirable knowledge of biological mechanisms that may be put to utility.

The systems described in the automated high-throughput biology laboratory 100 comprise a collection of automated workstation modules that may be inserted into or removed from a system and may be integrated into a control scheme whereby a user is able to program the activity of the modules for construction and performance of these assays.

Some of the features of the automated high-throughput biology laboratory 100 are properties and components that allow the systems described to be adaptable to a wide variety of assays of interest to those practiced in high-throughput biology.

Self-containment: The automated high-throughput biology laboratory 100 comprises a set of modular functional elements that is self-contained. The chemical reagents, chemical compounds to be screened, biochemicals and enzymes needed for particular reaction, cells, growth media, and other materials needed for the construction and performance of biological assays are all contained within the various workstations and modules of the automated high-throughput biology laboratory 100. The platforms used to store these items are transported to the different modules of the system for the performance of the different tasks needed to carry out an assay. This enables automation of an assay, in which once the reagents are brought to and stored in the system, the subsequent tasks needed are robotically performed.

Modularity and integration of components: The different modules are specialized to perform a particular type of task, and are insertable and removable from the automated high-throughput biology laboratory 100 so that needed functionality can be brought to the system and unneeded functionality is unable to interrupt the work flow with extraneous requirements. A system configured with a set of modules is self-contained in that a single control program run on a computer 165 enables a user to determine and enter the parameters needed for the operations of each module to the controller for that module. This allows the coordination of activities of different modules so that an assay can be constructed and performed in a seamless flow of steps. Activities requiring a coordinated action between several modules or groups of modules can be staged from a single set of controls in which the workflow is set up and then allowed to proceed in an automated manner.

Insertability and removability of modules in a self-contained system requires that the code necessary to communicate with or operate any module that can be made available to the system is stored in some location accessible to the controlling program, such as in a hard disk file, for example a hard disk on a computer 165. A module is inserted physically by bringing entrance and exit ports of the module to a location where they are available for access to the plate handling apparatus of the system, such as a robot arm delivering multiwell assay plates to and from a plate transport, and by connecting the module's logical communication hardware to the communication hardware serving the system controller. The system controller polls the status of every module with which it communicates. The presence of a new module, and absence of a previously detected module, provides notification for the controller to access the stored code that handles communication and transaction between the controller and the module. The controller references the block of programmed information that provides communication with the inserted module and frees the code block pertaining to the removed module. This new block provides the procedures and functions needed to pass parameters to the module controller, and also is referenced to provide the needed graphical objects by which the user enters the operational data for the module through a displayed form, window or other method of graphically-based data input.

In one embodiment, the system controller and module controllers communicate with code formatted in the Distributed Component Object Model (Microsoft, Inc., Redmond, Wash.). This establishes a direct stream of data between the system controller and each module controller to handle the active communication, such as passing numerical parameters to the module from the user and notification of the system controller of the operational status of each module. The system controller thus coordinates the action of the multiple modules by acting as a server, maintaining a list of the order in which each module needs to be activated in the construction and performance of an assay and sending the required parameters to each module when it is needed. This allows the user to operate any configured system from a single user interface on the control computer, in which only the modules presently in the system present windows, forms, or panels for data entry or other operating actions.

High-density multiwell platforms: Another feature of the automated high-throughput biology laboratory 100 is that each module is specialized to handle multiwell platforms such as microtiter plates that contain a high density of miniaturized wells. These multiwell arrays are constructed with dimensions conforming to an industry-standard format in which the center-to-center spacing of the wells is an integer subdivision of the standard 96 well (8×12 well) array with center-to-center spacing of 9 mm. For example, the 384-well plate is configured as an array in which the 8×12 standard array is subdivided by 2 to provide a 16×24 array of wells with center-to-center spacing of 4.5 mm. In one embodiment, the modules of the present invention are designed to accommodate plates with 1536, 3456, or greater number of wells, as disclosed in U.S. Pat. No. 6,517,781. Thus, the 8×12 well array with 9 mm center-to-center spacing is subdivided by 4 in the case of the 1536-well plate to provide an array of 32×48 wells with 2.25 mm center-to-center spacing, whereas in the case of the 3456-well plate, the subdivisor is 6 to provide an array of 48×72 wells with center-to-center spacing of 1.5 mm. Each type of high-density multiwell platform is specified by the well-to-well center-to-center spacing or offset along each column or row of wells. This offset is the necessary parameter that is required for a robotic plate positioning apparatus, such as a pair of X-Y linear actuators, in a module to address each well in a plate. The offset may be passed directly from the system controller to a module controller as a parameter, or a plate code may be passed instead, in which case the module controller would reference the offset from the set of data stored for each type of plate. The high-density well arrays of these platforms provide miniaturized sample volumes for the assays, with total liquid volumes in each well of less than 5 µL. This enables over 1000 assay samples to be constructed on a single platform so that the signals arising from the assay in each well can be read either in parallel or in rapid sequence by a measurement module. This achieves the ability to perform assay construction and measurement with high throughput.

There are several non-obvious advantages of the high-density plates manufactured according to the standards. The large number of wells in each plate allows logical subdivision of the wells into categories according to the experimental design and this template can be replicated numerous times on each plate. This has the advantage of enabling complete assay experiments to be run entirely on single plate with as many replicates or nested variable cells as are needed to derive statistical significance of an effect. For example, a 3456-well plate consists logically of a grid of 96 matices each consisting of 36 wells arranged in a 6 well×6 well square. Each well in each grid can be assigned an experimental condition needed to obtain experimental validity, and this assignment can be replicated for each grid. This has the advantage with respect to liquid handling, for example, of using a dispenser head having a lower density of individual fluid dispensing tips than the multiwell plate. In the case of a 96-tip dispenser consisting of a 12 tip×8 tip array with 9 mm center-to-center spacing, for example, that is used to dispense a particular control reagent to only one or several of the wells in an assay set, then these wells can be assigned to the same corresponding locations in each 6 well×6 well grid such that the dispenser needs to visit only that one or those several receiving wells in the grid. The plate receives that reagent and each of those receiving wells is addressed in a single pass of the plate.

Topographical mapping of assays on a single platform: Another feature of the automated high-throughput biology laboratory 100 is the ability to map topographically the different control and treatment samples to different wells on the same multiwell platform. This is afforded by the large number of miniaturized wells contained within a single plate, such as 1536, 3456, or greater number of wells. All the different sample conditions needed to perform an assay, such as the positive and negative controls, instrumentation or sample constituent controls, or the different concentrations of test compounds or biological modulatory agents, are all assigned in a logical manner to different wells in a plate. Furthermore, these assignments are easily retrievable by the user through the system controller so that the sample condition of any given well is always known as it proceeds through the sequence of steps necessary to construct and measure an assay. In addition, the different wells assigned to contain the same or the same type of sample (e.g., a given, fixed dilution of a compound or reagent) are easily accessed.

Figure 2:
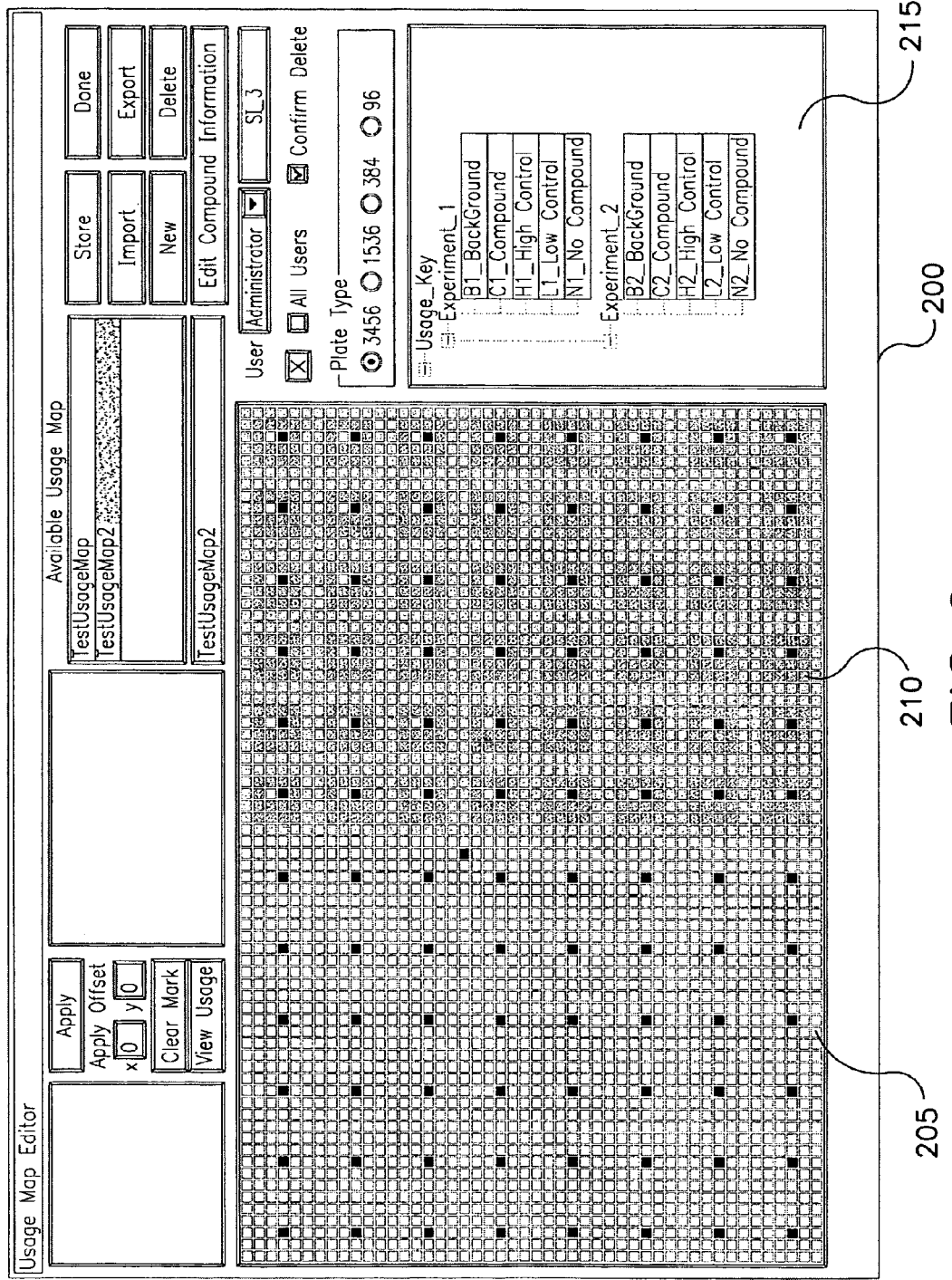
FIG. 2 shows one embodiment of a graphical user interface showing mapping of a high-density microplate.

Topographical mapping of an assay is necessary to handle the abundant information produced by having many assay samples or replicates of the same assay condition contained within a high-density multiwell platform. This is illustrated in FIG. 2, which is the Usage Map Editor form of the graphical user interface 200 presented by a system controller 165. A map of a 3456-well plate (48×72 wells) is shown divided into 2 sections 205 and 210. Different chemical compound screening experiments are performed on the same plate; the 48×36 well grid 205 on the left is to be used for the first experiment, while the 48×36 well grid on the right 210 (shaded darker) is to be used for the second experiment. For example, the first experiment may be an assay for inhibition by a chemical compound of the activation of the muscarinic cholinergic receptor M3, while the second experiment may be an assay for inhibition of a $\beta_2$-adrenergic receptor. These assays differ in the types of cells used to assay receptor inhibition and in the corresponding reagents and pharmacological agents needed to perform each assay. Nonetheless, the assays can be designed to screen the same set of chemical compounds in the 2 different assays using the same liquid transfer and spectrometric measurement modules, and, hence, are suitable for construction on the same plate. Each assay in each section is mapped to a square array of 36 adjacent wells (6×6 wells), and the sample condition of each well is indicated by the gray shading. The key to the usage map is illustrated in the panel 215 at the lower right of the form. All wells with the same assay sample condition are shaded the same level of gray in the map, and the text in the panel indicating each assay sample condition is highlighted against a background of the same gray level as well in the map. For the 2 different experiments, these gray levels are different even for similar conditions, such as low or high receptor activator concentrations, low or high concentrations of the chemical tested in each 6×6 well grid, and the negative and positive controls. The system controller parses the plate usage map to the lists of parameters needed by the various modules of the system so that the correct reagents and compounds are added to each well. The advantage of the usage map is that it enables the different modules to coordinate their handling of the plate using a unified list of information so that the assay samples are constructed correctly, the signal read from each well is assigned to the proper well, and the results of the assay can be analyzed in a convenient and easy to understand way.

The same capability of topographic mapping of multiwell plates also provides the ability to manage the storage of different chemical compounds or reagents in the many different wells of a high-density plate. Each compound may be assigned an identifier that is then mapped to a well location and may then be used to retrieve the compound from a usage map listing. This enables the millions of chemical compounds that may be desired to be tested for therapeutic activity to be maintained and accessed by the same automation elements used to stage the assays on high-density plates.

Acoustic Radiation Pressure control "acoustic control" of diverse functions: Another feature of the automated high-throughput biology laboratory 100 is the incorporation of acoustic control in different modules to handle several important tasks of assay performance. One of most important tasks in the construction of miniaturized assays which may have total liquid sample volumes of 1 µL is the volumetric dispensing of liquid samples such as chemical compounds, assay reagents, signal development reagents or other chemicals in which the total volume added to each sample well is less than 10 nL. One mechanism for dispensing volumes of this range is acoustic ink-jet dispensing in which surface acoustic wave control is used to dispense single or multiple liquid drops of the necessary volume, as disclosed in U.S. Pat. No. 4,751,530. In surface acoustic wave control, the air-liquid interface of a sample in a container is energized to a stationary wave mode by applying mechanical vibration to the container of a particular frequency. This stationary wave mode is then made unstable by the superposition of a brief (1 µsec) pulse or mixed frequency stimulus. The instability results in the collapse of the stationary surface elastic wave to a single mode in the form of an extrusion of a small part of the liquid surface away from the remainder of the liquid surface. When the pulse is of sufficient magnitude, the instability collapses into a drop that is ejected away from the interface along the normal axis of the surface. The volume of the ejected drop is determined by the amplitude and frequency composition of the stimulus. One type of this dispenser is disclosed in U.S. Pat. No. 6,596,239, the contents of which are incorporated by reference in their entirety, and commercially available as an integratable modular unit from EDC Biosystems, Inc., Mountain View, Calif.

Figure 3:
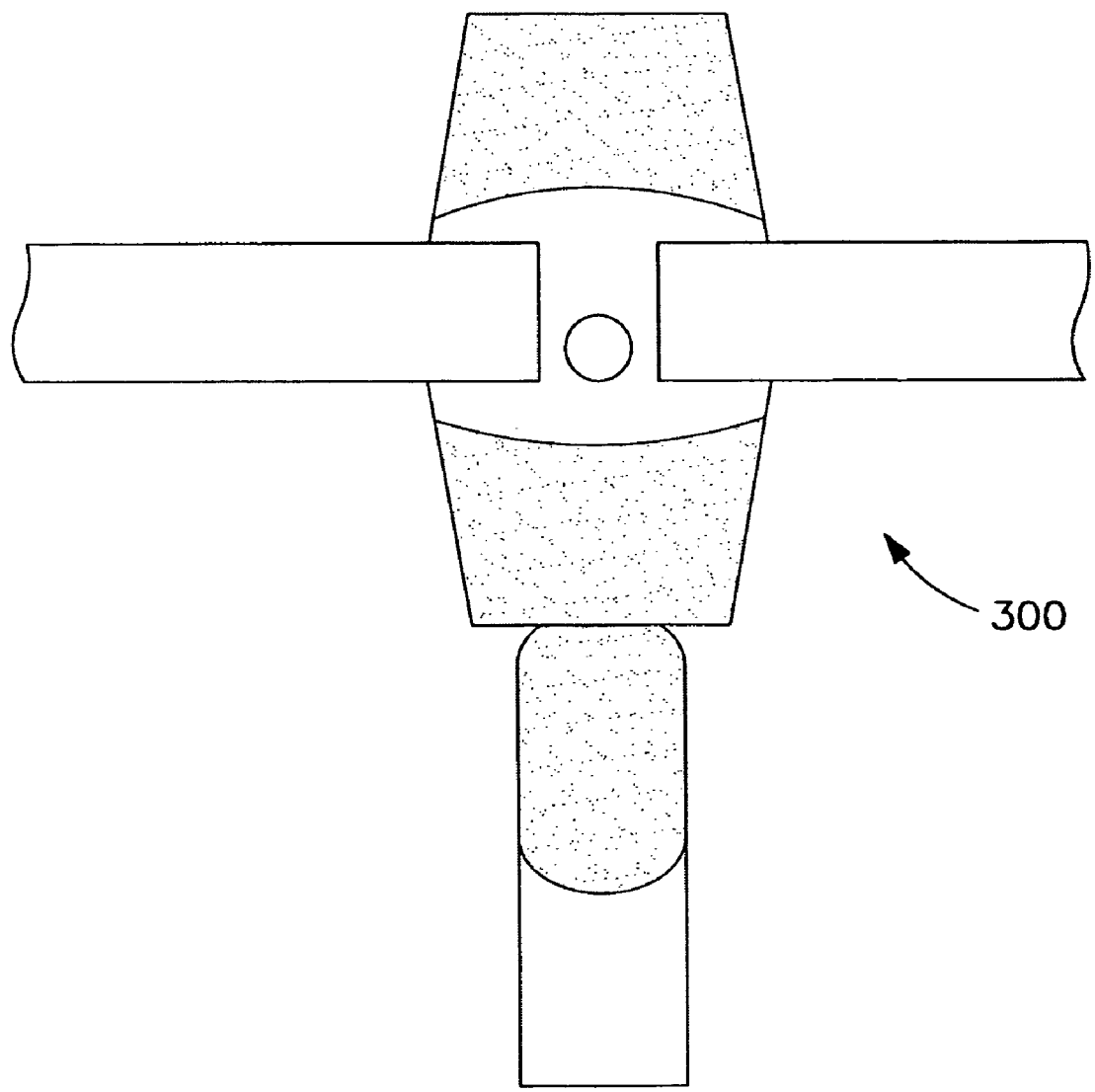
FIG. 3 shows a sectional view of one embodiment of a dispenser.

With reference to FIG. 3, the EDC Biosystems module uses a flowing liquid fountain 300 to couple a stationary acoustic generator and lens to the bottom surface of the multiwell plate containing the liquids to be dispensed which is used as the source plate. The platform is positioned by the use of a robotic X-Y positioner so that the lens is centered under the bottom of each well in the platform and the dispense actuation stimulus is applied to eject the programmed volume of liquid upwards away from the surface of the liquid in the well. The multiwell plate used as the destination for the dispensed drops is inverted and mounted to the source plate and aligned such that the center of each destination well is vertically positioned over its corresponding source well. Fiducial markings and features such as indentations and protrusions are incorporated into the flanges and facing surfaces of the high-density multiwell platforms to allow alignment to be achieved simply by laying one plate on top of another and clamping the pair into the platform caddy or nest used to fixture the plates to the robotic positioner. The drops ejected by the acoustic stimulus are typically of volumes less than 10 nL and are accurate and reproducible. The actuation parameters can be adjusted to achieve drops in the range of 1 pL as can be dispensed by other means of subnanoliter-volume liquid dispensing such as piezoelectric or thermally actuated ink-jetting technologies. This type of acoustic dispenser is one example of means for quantitatively transferring very small volumes of chemical reagents from a source platform to a platform in which assays are under construction. An additional use of this type of dispenser is transferring a small volume of an assay sample to a substrate for subsequent analysis. For example, the constituents of the cells in an assay sample may be released to and dispersed within the liquid assay sample, and then dispensed by acoustic means to a matrix substrate for time-of-flight mass spectrometric analysis. This enables the analysis of changes in protein, carbohydrate or other molecular constituent levels in the cells brought about during the assay.

Acoustic control is also implemented by extending the utility of sound-generating devices such as the HTS-01 (EDC Biosystems, Inc, Mountain View, Calif.). For example, the piezoelectric actuator component of the acoustic lens also serves as an acoustic transducer of the mechanical vibration evoked by elastic excitation of a well. The fundamental frequency of this elastic vibration is proportional to the length over which the vibration travels, and hence, is determined by the height of the liquid sample in the wells. Analysis of this fundamental frequency by heterodyning, spectrum analysis, or other means known to those skilled in the art enables determination of the volume of liquid sample in the well. This information may then be used for subsequent stoichiometric calculation at other steps in the construction of an assay (i.e., how much of a subsequent reagent to add) or determining whether a sample assay is present in a well.

Another use for acoustic control is ultrasonic vibration of the liquid contents of a well. In this case, the vibration frequency applied to a well is a substantial multiple of the fundamental frequency determined by the dimensions of the well contents. This causes the liquid contents to undergo considerable compressional vibration, depending on the amplitude of the high-frequency (e.g., 1 MHz) vibration applied to the sample in the well.

One use for ultrasonic excitation is dissolution of solid materials added to the liquid contents of the well and mixing of the dissolved compound to homogeneity throughout the well contents. Another use for ultrasonic excitation would be to stop the reactions occurring in an assay at a particular desired time after initiation of the assay by ultrasonic disruption of the cells. This would achieve a "fixation" in the state of the cells in that the cells would be disrupted and their contents distributed throughout the liquid contents of the sample such that the cellular reactions occurring during the assay would be diluted and their kinetics decreased. For example, in an assay for the activity of a cellular kinase, the assay would be allowed to proceed for a period of time, and then the ultrasonic excitation would be applied to disrupt the cells to stop the phosphorylation of cellular substrate by the kinase by the dispersion of the cellular contents into the sample volume. This would fix the phosphorylation reaction an enable the phosphorylated substrate to be extracted, purified, and analyzed to determine the activity of the kinase in the assay. The assay could be performed in the extracellular presence of a membrane-impermeant phosphatase inhibitor to prevent changes in the phosphorylation state of the substrate after cellular disruption if needed.

Another use for ultrasound in biological assays is to stage a second reaction in a sample well after an initial assay is constructed and allowed to proceed to an endpoint of the assay. For example, in a gene expression assay evaluating the changes in RNA transcript levels in response to the addition of a modulatory compound, the assay could first be allowed to proceed with the cells in their growth medium and in the presence of the compound, and then fixed by ultrasonic disruption of the cells. The second reaction, reverse transcription-polymerase chain reaction (RT-PCR) to prepare the transcripts for sequencing and analysis, could be staged by adding the ribonuclease inhibitors and enzymes and reagents needed for RT-PCR to the sample well immediately prior to fixation of the modulatory activity in the cells by ultrasonic disruption. The RT-PCR reaction would then be able to proceed after the disruption of the cells in the same sample in which the initial modulatory reaction was carried out.

Handling different ranges of liquid volumes: In some embodiments, the automated high-throughput biology laboratory 100 may relegate the transfer of different ranges of volumes to different modules. For example, the sub-nanoliter range of liquid volumes, which is typically used to dispense concentrates of chemical compounds or other rare, expensive chemical reagents to assay samples during construction, can be handled by the acoustic dispensing module already described. Other ranges of volumes are handled by other modules. For example, sample volumes greater than 2 µL (to >200 µL) are routinely handled by widely available robotic liquid transfer devices such as the Sciclone (Zymark, Inc., Woburn, Mass.). Volumes in this range are typically used in the preparation of bulk volumes (e.g., 25 µL) of intermediate dilutions of chemical compounds and reagents in low density multiwell plates such as 96- or 384-well plates, which are then transferred to high-density multiwell platforms during assay construction.

Volumetric liquid dispensing in the range of 10 nL to 2 µL is routinely done using solenoid valve actuators. This method of dispensing is described in U.S. Pat. No. 5,985,214 as an application for delivering the reagents needed to construct an assay to a large number of wells (e.g., 48 wells) simultaneously in high-density multiwell plates. In U.S. Pat. No. 5,985,214, the dispense orifices are fixtured in a row, and the dispensing through each orifice is controlled by a respective solenoid valve connected to the orifice by a small-diameter stainless steel tube. Each solenoid valve is fed by a supply tube connected to a manifold that, in turn, is connected to a liquid reservoir supplying the chemical reagent, cell suspension, or other liquid which is provided to all dispensers in the fixture. Multiple fixtures of dispensers, each connected to a different liquid supply reservoir, were used to construct the assays in the plates when different liquids needed to be dispensed to each well in the plate to construct an assay.

In some embodiments, the automated high-throughput biology laboratory 100 uses a modification of the method described in U.S. Pat. No. 5,985,214 as a preferred embodiment. Each dispenser orifice is constructed from a 1-mm diameter cylindrical piece of sapphire in which the back end is hollowed out in a conical shape at a 45° taper. A 0.2-mm diameter hole drilled through the cylinder provides the dispenser orifice. The sapphire piece is mounted at one end of a 1 mm ID stainless steel tube that is connected to the outlet of a solenoid valve, such as the INKAH (The Lee Company). Four of these orifices are fixtured together in a 2×2 square array such that the center-to-center spacing between the orifices in a row or column matches the center-to-center spacing of the wells in the target plate (e.g., 2.25 mm for a 1536 well plate or 1.5 mm for a 3456 well plate). The inlet of each solenoid valve is fed by a separate supply bottle, so that the four supply bottles used for this four-dispenser array can supply different liquid reagents or other fluids needed to construct an assay, or they can be used to supply the same liquid to the dispensers with each dispenser servicing a different well in a plate. Each supply bottle is pressurized to drive the liquid toward its respective solenoid valve. Dispensing is controlled by a shaped pulse delivered by a separate driving circuit for each solenoid valve. An initial opening pulse consisting of a 40 V 0.5 msec duration opening pulse is followed by a variable duration holding voltage of 10 V. The duration of the holding voltage determines the volume of liquid dispensed through the orifice. The waveform can be stored in a static random-access memory (sRAM) as a digitized encoding of the desired pulse, and then delivered to the solenoid valve after digital-to-analog conversion and amplitude scaling by an operational amplifier. Readout of the sRAM can be implemented by enablement with a set signal from a D-type flip-flop actuated by the dispenser controller. The wells of a high-density plate are filled with the reagents by using an X-Y translation table to position each well under each dispenser orifice. The velocity of the translation table and the linear position of each well are coordinated with the frequency at which the actuation pulses are delivered to each solenoid valve by the dispenser controller. This ensures that dispense actuation occurs when a well is positioned under the orifice of the dispenser. The dispenser controller parses the usage map into the pattern of actuation needed to deliver the correct liquids to the wells in the construction of an assay.

The modularity of the automated high-throughput biology laboratory 100 allows the different instruments that handle different volume ranges of liquid transfer to be brought to an assay or removed when they are not needed and replaced by other modules performing different tasks.

Kinetic assays: The integrated modularity of the automated high-throughput biology laboratory 100 enables combining different tasks into a module to provide new functions. An example is integration of liquid handling and spectrometric measurement with robotic multiwell platform positioning having high spatial resolution for kinetic assays. In kinetic assays, the signal produced by the assay is read as a function of time, and the time course of the assay signal is the parameter of the reaction that is measured. Most assays, by contrast, are endpoint assays, in which the signal generated by the assay is measured at a single fixed period of time after the assay is initiated and allowed to proceed. Kinetic assays can be devised by running endpoint assays in replicated samples in which each sample is stopped at a different time and its signal read. The disadvantage is that the time course determined from the multiple samples incorporates the intrinsic variability of the assay, which is the variation of the assay when replicated samples are run and then measured at the same endpoint. The advantage of performing kinetic measurements by reading the assay signal from each sample at multiple points in time is that the time course variability is obtained directly and without possibly incorrect inference of this variation from the endpoint measurement. In addition, kinetic assays provide greater information about biological mechanisms underpinning an assay and the source by which a modulator or test agent acts on the biological processes probed by the assay. For example, analysis of endpoint assays is typically calculation of an equilibrium or steady-state distribution constant, such as an EC50 or IC50, the concentration of agent or modulator that results in a 50% change in an assay. Kinetic assays can be analyzed to provide rate constants of the biological process reactions probed by the assay, which provide greater detail about the mechanism by which an agent or modulator may act to produce its effect. As is know to those skilled in the art, numerous devices have been invented that enable performance of kinetic assays in multiwell platforms, such as the Fluorescent Ion Probe Reader (FLIPR, Molecular Dynamics Corp., Sunnyvale, Calif.). These devices either use low-density multiwell platforms (e.g., 96-well or 384-well plates) and are not capable of being inexpensively extended to high-density platforms or custom, specialized microfluidic platforms that are not able to be used with robotic instrumentation designed for use with the industry-standard multiwell platform format (e.g., Aviva Biosciences, San Diego, Calif.) without modification. The present invention incorporates a kinetic assay module derived by the simple integration of submicoliter fluid handling and high-sensitivity spectrometric measurement components from standard modules that normally handle these tasks separately.

One embodiment for kinetic assays for use in the automated high-throughput biology laboratory 100 is a module in which the multiwell plate scanner with multiple wavelength spectrometric optical head described in U.S. Pat. No. 6,586,257 is combined with the reagent dispenser described in the section "Handling different ranges of liquid volumes", discussed above. The high-density multiwell platform is positioned in the horizontal plane by an X-Y translation stage which allows each well to visit the dispenser head where fluid can be delivered to the well from the top. The same stage allows spectrometry (e.g., multiple wavelength fluorescence) to be performed from the bottom by positioning the clear bottom of the well over the optical head. The dispensing and optical heads are fixtured to separate Z-axis positioners to enable them to be located at their needed locations above the top of the well and below the well bottom, respectively. For example, the dispense head is typically fixed at 1 to 5 mm above the upper surface of the multiwell plate, while the optical head is typically brought to a distance of <0.5 mm below the clear bottom surface of the well.

In one embodiment, the detector of the signal originating from the assay is specialized to provide high sensitivity and wide dynamic range to the extent of being able to detect the emission from a single fluorogenic molecule in the case of fluorescence assays. The optical read head described in U.S. Pat. No. 6,586,257 for high-density multiwell platforms with dark interstitial material between the wells and clear well bottoms comprises a sensitive spectrometric system. The materials used to construct the wells have a high transmissivity and low intrinsic fluorescence in the ranges of light wavelengths used in biological assays employing fluorescence. These ranges typically are light between wavelengths of 350 to 600 nm for excitation and 400 to 800 nm for emission. These material properties allow high light irradiance to be used for illumination, e.g., >1 W/cm$^2$, so that the fluorophores are efficiently excited at a high rate (>$10^4$ s$^{-1}$). Thus the fluorophore emission is bright compared to the background and provides a large signal when recorded with a sensitive detector such as a photomultiplier tube. Integration of the detector signal over intervals of time such as 1,4,20, or 50 msec during the period in which the head is under the well window provided by the clear bottom also improves signal detection by averaging uncorrelated noise and by enabling subtraction of any readings unassociated with the assay obtained when the head is between wells. The lens of the optical read head is located within a few tenths of a millimeter from the well bottom to provide a relatively large numerical aperture and, hence, efficient capture of the assay emission without contamination by emission from adjacent wells. Low attenuation by the fiber optic transmission pathway and by the interference filter over the range of light wavelengths passed also provides high sensitivity. The sensitivity and dynamic range of the optical subsystem are combined with high-resolution spatial positioning and microliter-scale dispensing actuation controlled on a millisecond timescale to enable kinetic assay measurements in a single module.

Figure 4A:
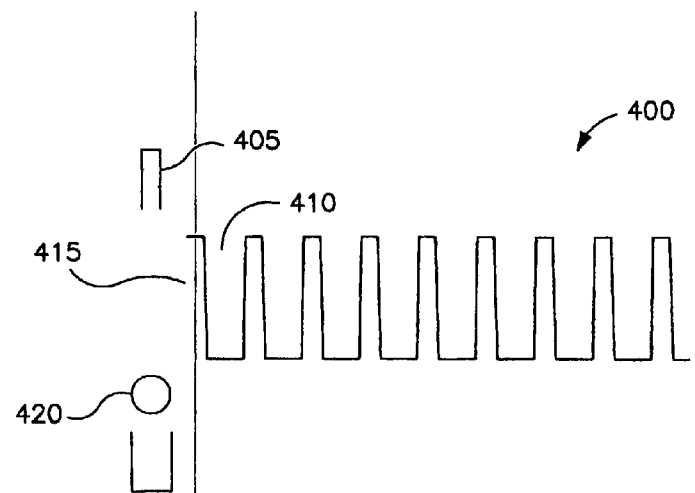
FIGS. 4a-4d show a general kinetic assay.
Figure 4B:
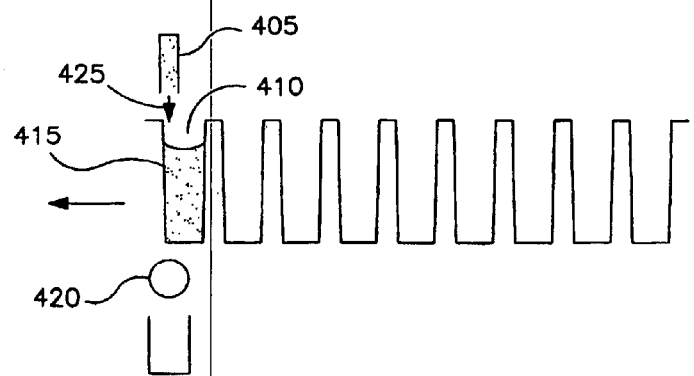
Figure 4C:
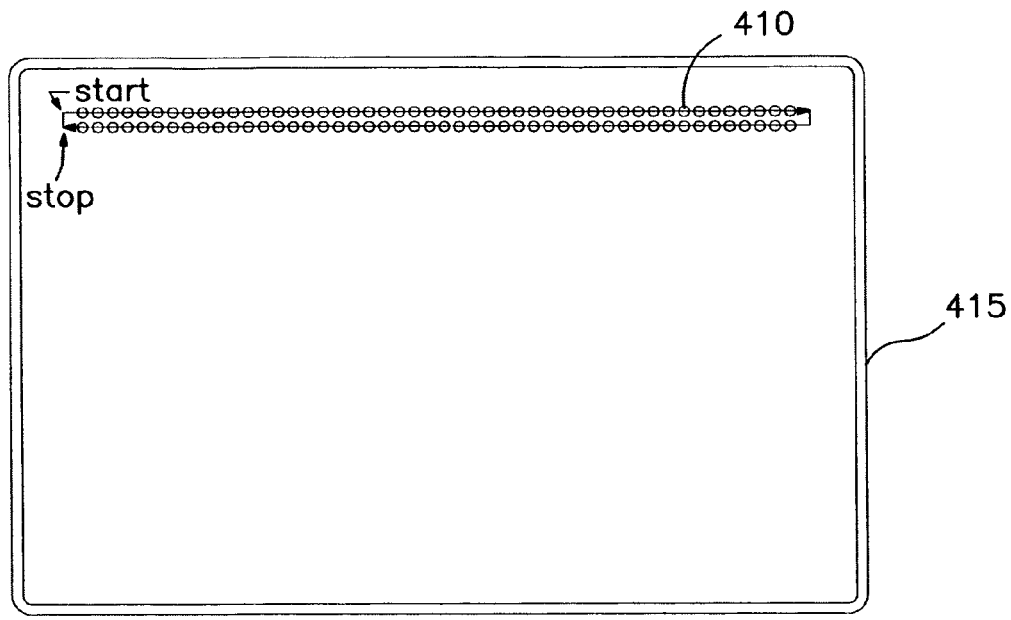

One embodiment of a general kinetic assay using the integrated module 400 is outlined in FIGS. 4a-4d. FIG. 4a depicts the arrangement of a dispenser head 405 located above a row of wells 410 on a plate 415 and a optical head 420 directly below the wells 410. Although the wells 410 are depicted empty, it is understood by those skilled in the art that most components of the assay may already be constructed in the wells with cells, cell growth media, buffers, assay reagents, assay signal development reagents, test chemical compounds, or other assay components either with this dispenser or with dispensers located in different fluid-handling modules. In some assays, test chemical compounds would be added to the plate wells by a sub-nanoliter range dispenser, and the plate would be transferred to a different dispensing module for the addition of cells, buffers, media, or reagents. Then the plate would be transferred to the kinetic assay module to receive the reagents affecting the time course of signal generation by the assay, such as activators, modulators or other signaling compounds that trigger the onset of the reaction measured by the assay, from the dispenser depicted above the row of wells. FIG. 4b depicts the operation of the module. The plate 415 is moved horizontally between the dispensing 405 and reading 420 heads, and the dispenser 405 dispenses an assay activator 425 while the optical head 420 reads the resulting assay signal. Depending on the expected kinetics of the assay, the time between dispensing to a well and reading the assay can be varied so that the time course of the reaction can be followed. One way to obtain this phasing is depicted in FIG. 4c, which shows 2 rows of a 1536-well plate 415 with 48 wells 410 in each row. With typical linear translation stages, one row of wells can be swept under the dispenser orifice in 2 sec. A round trip scan can be constructed in which the plate is first moved from left to right with the dispenser head positioned over the line connecting the centers of the top row of wells. The positioner is then indexed at column 48 to position the head over the line connecting the centers of the second rows of wells, and the plate is moved from right to left until column one is under the head. The round trip requires about 4 sec, which provides the temporal resolution of the kinetic assay conducted using this scheme.

Figure 4D:
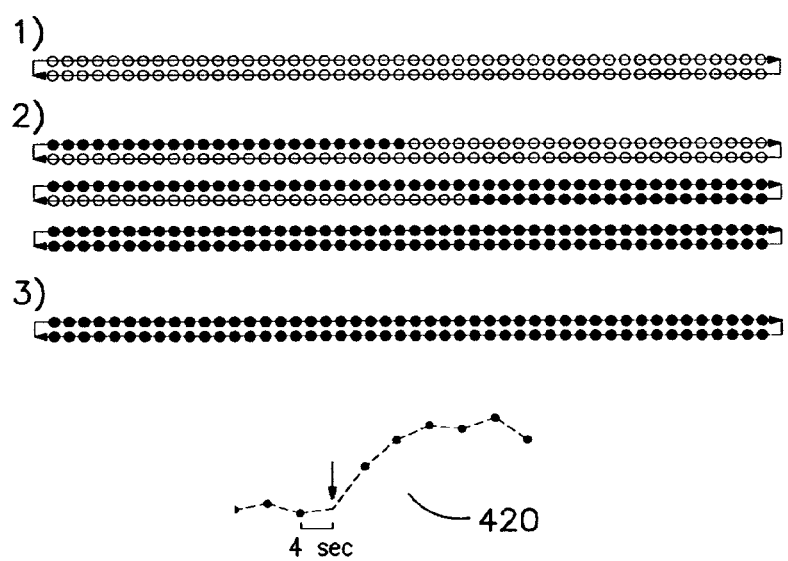

FIG. 4d depicts an example assay. In the top panel 1) of FIG. 4, a series of roundtrip scan reads of the 96 wells in the 2 rows using the optical head is obtained to establish a background signal for each well. At time zero, a single roundtrip scan is used to dispense the assay activator to each well and a simultaneous optical read obtains the zero-time assay signal for each well. Then a series of assay scans is performed, in which each well is read during each scan. This results in a timecourse 420 of assay signal reads for each well, in which the signal for each well is read 4 sec after the prior read, and the timecourse of assay progression is measured for as long as needed. In this example, 96 replicate timecourses of the same assay can be obtained, or if different assays are initially constructed in the different wells, then the effects of variations in assay composition on assay kinetics can be determined. Since only 2 rows of wells are used for this kinetic assay, multiple assays can be performed using the same plate repositioned to bring another 2 rows under the dispensing head.

This scheme can be widely adapted to different types of assays with very different kinetics. For example, since the total scanning and reading time for each well is on the order of 40 msec, fast kinetics can be followed by confining the plate positioning to a contiguous path of a smaller number of wells, such as a grid of 2×2 wells or even one well if the plate is held stationary and the integration period of the photodetector is made very brief. Long timecourses, such as changes in transcript levels of expressed genes can also be followed by varying the number of rows visited during the scan which, in turn, increases the period of time between successive reads of the same well. For example, a 1536-well plate requires about 11 minutes to scan every well using a serpentine motion. Thus, the time course of gene expression using a fluorescent readout marker such as Green Fluorescent Protein or β-lactamase could be tracked in every well in 11 minute increments for 2 hours with 12 complete roundtrip scans.

Applications of the invention: The invention is suitable for the parallel staging of a wide variety of assays in miniaturized format. These assays include, but are not limited to, those that provide spectrometric readouts. Assays may be designed to measure biochemical reactions, such as the inhibition or potentiation of enzymatic activity, such as cytochrome P-450, a major detoxifying enzyme of liver (see U.S. Pat. No. 6,514,687). Assays may also incorporate the various manipulations required for molecular biology, including, but not limited to reverse transcription, polymerase chain reaction, nucleic acid hybridization, restriction enzyme digestion and fragment analysis, nucleic acid separation by electrophoretic mobility, fragment ligation and vector construction, nucleic acid sequencing, or analysis of gene expression. Because many individual assays can be staged on single, high-density multiwell plate, the system described enables performance of the same types of gene expression analysis presently performed with nucleic acid microarrays. High-throughput microarray analysis is available commercially from GeneXP Biosciences. One advantage of the present invention is that distinct nucleic sequences can be confined to individual miniaturized wells. Thus there is no need to confine the distinct sequences to discrete locations on a single substrate in which all locations are contacted by a common liquid medium, as is the case with microarrays. This eliminates the need to spot the same nucleic acid sequence at multiple different locations on the array, which is required to ensure that the signal arising from a given spot is not due to contamination by sequences from neighboring locations. In the multiwell plate, each distinct sequence pool is physically isolated from its neighbors, and never comes into common fluid contact, a major source of cross-contamination of microarrays constructed with spots.

The flexibility afforded by the present invention in conducting microarray assays in high-density multiwell plates also extends to kinetic analysis of gene expression including the simultaneous monitoring of the expression of multiple genes. Each well in a high-density multiwell plate provides a discrete sample container for up to ~10,000 cells. Since only very small volumes, e.g., 10 nL, of cell concentrate modulators need to be added to a well in order to activate a particular physiological response in cells, such as triggering of gene expression control elements, all cells in a well are synchronized in their response to the modulator. A kinetic analysis of the expression of multiple genes could thus be performed by using a block of multiple wells all containing essentially the same staged assay. At different times following the initiation of the response to the modulator, the contents of a column of wells could be processed, such as by reverse transcription-polymerase chain reaction or base labeling with fluorophore or other processing reactions, for counting the number of specific message transcripts. In this design, each well in a column would be processed for the transcripts resulting from the expression of a different gene. Each column in the block would comprise a time point at which the expression levels of the target genes would be measured. The contents of these wells would be transferred to a second high-density multiwell plate in which the transcript counting would be performed, such as by hybridization to sequences of the target genes under analysis using fluorophore displacement dequenching or other techniques known to those skilled in the art. The result would be a kinetic profile of multiple gene expression in which the columns of wells would represent the time course of gene expression and the rows in each column would track a specific gene. Since this assay would involve only routine microfluidic handling and spectrometric measurement, this type of analysis would be easily performed using the present invention.

Analysis of multiple gene expression time courses opens the avenue to the design of new assays in chemical compound screening for discovery of new therapeutics or other uses of high-throughput biological assays. Among the key targets of interest in drug discovery are signal transduction pathways in cells that are activated or inhibited by the binding of ligands such as neurotransmitters, hormones, cytokines, or other extracellular modulators to membrane receptors. These receptors in turn activate of inhibit the activities of a wide variety of intracellular modulators of biochemical activity such as heterotrimeric G proteins, kinases, proteins that control the expression of genes, or other modulatory factors. A critical need for application of the sequencing data gathered by the Human Genome Project is the functional linkage of gene products and control elements into biochemical circuits. That is, it is now necessary to discover and organize the relationships between the different gene products into functional pathways. Because the present invention incorporates routine assay staging in high-density multiwell plates, it is uniquely suited to this challenge by monitoring the expression of a large number of genes over time. This will enable changes in the entire physiological state of a cell to be measured in response to a biological modulator or to a potential therapeutic agent.

The present invention is useful for new methods for elucidating the function of gene products, such as the generation and analysis of cells in which the product of a single gene or multiple genes are knocked out by RNA interference. RNA interference is naturally occurring process in which a double-stranded small RNA 19 to 23 base pairs in length that contains sequence complementary on its sense strand to the 5' end of a naturally expressed messenger RNA will cause the degradation of that mRNA. Thus, the presence of the interfering RNA will effectively knock out a gene's product. Synthesized small interfering RNAs (siRNA) have become a new technology for understanding the function of individual genes, and for understanding the functional interactions between gene products comprising biochemical pathways in cells. The present invention provides a useful system for staging siRNA knockout assays particularly complex assays in which multiple genes are targeted in each cell.

For example, a standard assay developed for the present system utilizes control of expression of a gene for the bacterial enzyme β-lactamase. This gene is inserted in a vector downstream from a gene expression control element such as CREB, NFκB, NFAT or other regulatory element. This vector is then used to transfect a cell line in which the activity of a signal transduction pathway, which either endogenously occurs or that has been constructed by transfection with other vectors, results in the activation of that genetic control element. Thus, when the signal transduction pathway is activated, the reporter β-lactamase is expressed, which can be detected by its cleavage of the fluorescence resonance energy transfer probe CCF4. Example signal transduction pathways include those regulated by such cell surface receptors such as the muscarinic cholinergic receptor M3, the PPARγ receptor, IFN or other cytokine receptors, or many others. Cell lines constructed to provide a β-lactamase readout of a signal transduction pathway are termed "biosensors".

A gene knockout experiment in the present invention using siRNA would test the extent to which the targeted gene's product is involved in the signal transduction pathway. Such involvement could be weak, due to its presence in a peripheral part of the pathway, or strong due to it being a direct link between the cell surface receptor and other elements in the main pathway. Because the high-density multiwell plate enables staging a large number of assays on a single platform, a large number of different experiments could be conducted simultaneously using the present invention. For example, the siRNA for the target gene would be synthesized and then added to a large number of wells in a plate using acoustic dispensing. Then a wide variety of different cellular biosensors, each constructed to provide a β-lactamase expression readout of a different signal transduction or metabolic pathway, could be added to different wells of the plate using the solenoid-metered dispensers, and the siRNA introduced into the cells by electroporation (Gentronics Biomedical), cationic lipid, calcium shock, or other means applied to the appropriate wells. These different assays could be staged all at once on the same plate by adding the different modulators or activators of the signal transduction pathways only to the appropriate wells containing the cells constructed to provide readouts of those pathways. The wells would be coded according to the plate usage map, and the involvement of the targeted gene could be determined from whether the siRNA exerted any effect on the normal readout of each assay. Due to the large number of wells, all positive and negative controls, including those using scrambled RNA sequences to disrupt the RNA interference, would be present on the same assay platform, so that the siRNA effect on each signal transduction pathway would be unambiguous. Determining the extent of mRNA inhibition produced by the siRNA could also be determined after the assay using the molecular biological protocols inherent to the present invention. In addition, the role of a particular product could be measured by characterizing the effects of a library of chemical compounds on the signal transduction pathway in the presence and absence of the targeted gene product. This would provide information as to the true molecular target of a chemical compound under development as a therapeutic.

To discover the roles of the products of multiple genes in a signal transduction pathway, multiple siRNAs would be designed and synthesized to knock out the products of different target genes in one or more biosensors. These different siRNAs would be introduced to individual populations of the biosensor to discern which targets comprise components of the signal transduction pathway. Then, siRNAs against different targets that individually are only weak or peripheral components could be combined in the same cell populations to measure the extent to which interactions between gene products are involved in the pathway. For example, the products of individual genes may provide functionally redundant or degenerate links in a signal transduction cascade so that the absence of one product may simply shunt the signal through a different path. Alternatively, two gene products may provide weak links individually, but together may cooperate through allostery or other association mechanism to provide the possibility of a strong link when both products are present together. In either case, knocking out both products in the same cell would be necessary to discern whether an apparently weak component of a path was actually a major component. The present invention enables the measurement of the extent of coupling between two gene products in a signal transduction or other metabolic pathway.

Thus, the present invention is uniquely suited to unraveling the molecular networks of cells and discovering how the products of individual genes are organized into functional systems underlying cellular physiology. The same invention is also useful in harnessing this information to the discovery of new therapeutic agents directed toward newly discovered components of these molecular systems. In summary, the present invention provides for the systematic discovery and usage of new biological assays in a self-contained, expandable format with complete management of the information therein derived.

Automated High-throughput Screening Laboratory for RNA Interference

In one embodiment, the invention is an automated high-throughput biology laboratory 100 of integrated functionality using high-density microtiter plates with miniaturized wells for determining the functions of specific expressed genes by the use of siRNA. The automated laboratory is useful for determining the roles of gene products in cellular molecular networks, for the discovery of molecular targets in biological mechanisms, the discovery of new therapeutic targets of disease, drug discovery, agricultural discovery, and other uses. The automated laboratory enables the construction and analysis of assays in which siRNA, designed to knock out the message of the target gene of interest, is introduced into cells of a line engineered to provide a quantitative readout indicating the activation, inhibition, or other modulation of one or more biochemical pathways. Because of the high density of wells in each plate, multiple assays using the same siRNA sequence can be performed using different engineered cells lines on the same plate, or different siRNA targets can be assayed using the same engineered cell line. The automated laboratory provides ultra-high-throughput analysis of gene function and is useful for discovering new therapeutic targets as well as screening chemical libraries for action on targets isolated by RNAi.

All functions needed for biological assays using siRNA are brought to the automated high-throughput biology laboratory system. The functions of the modular stations and the transport system are coordinated by a system controller with a graphical user interface that allows the user to set up and perform the siRNA assay. Some of these functions include the following:

i. Specification of the particular gene sequence whose product is to be knocked out;
ii. Designation of the biosensor cell type or types to be tested in the assay and, hence, the specific biochemical pathway to be probed in the experiment;
iii. The reagent and chemical composition of each well in the assay, including the presence or absence of specific activators, inhibitors, or other modulators of the pathway being probed, as well as chemical compounds from a library that can be tested for activity when the target is knocked out;
iv. The mode of assay readout, such as fluorescence, absorbance, or other modality, the selection of filters required for a particular spectrometric assay, or kinetic or end-point modes of reading.
v. The analysis of data, such as which signals from which wells are to be used as baselines or backgrounds, computations on signals from organized groups of wells with related sets of conditions to provide EC50, IC50, or other metrics, and other analytical functions.

The high density of wells and the ability to logically assign wells enables the relatively complicated experimental design needed for valid siRNA experiments to be efficaciously obtained. For example, in a typical siRNA experiment in which the siRNA is delivered to a biosensor cell line and an effect on that biosensor's pathway is assayed, numerous control experiments are needed. One control consists of the siRNA added to cells in the absence of a transfection reagent (e.g., a cationic lipid) to determine whether the knockout agent exerts any exogenous effects on that cell line in the absence of entry and knock out of the specific targeted message. Another control is the effect of the transfection reagent on the biosensor cell line in the absence of the siRNA. Still another control is for nonspecific effects of introduced short segments of dsRNA on the cell line, in which case a scrambled sequence of the siRNA, not complementary to the message desired to be knocked out, needs to be introduced into the cell line to control for the possibility of this nonspecific effect. Yet still another set of controls that need to be designed into the siRNA experiment includes the controls for previously listed nonspecific siRNA effects in the presence of activator of the pathway probed with the biosensor cell line. The high-density format of the multiwell plates used in this invention allows this plethora of controls to be organized on the same plate and in the same vicinity of the plate as the main experimental assay for the effect of the designed siRNA on the biosensor's activated pathway. The high-density microtiter plates with miniaturized wells thus provide economies both in the amount of reagents and other costly chemicals needed to perform each assay and in the ability to design complete experiments capable of isolating a true siRNA effect.

Chemical compound (siRNA) management—The automated high-throughput biology laboratory incorporates chemical compound management as a fundamental resource to control the gene sequences targeted by siRNA and to integrate the data produced by an assay into information about the role of a target gene sequence in a biochemical pathway. Compound management is a 3-tiered organization of functions and analysis that allows ultra-high-throughput assay data to be managed so that information about the particular biochemical entities of interest, whether chemical compounds in libraries or a multitude of siRNA sequences targeted to particular gene products, can be derived. It also provides information regarding the location and quality of each entity to the control system used to design assays, such as the plate, well, quantity, and dilution of a particular reagent.

The first tier consists of a set of databases in which each record contains information pertinent to the design and construction of assays. For example, with respect to siRNA, one database consists of all the siRNA sequences designed to knock out particular targets of interest. Each record contains the plate identifier, well identifier, concentration, and volume of each siRNA that has been designed, synthesized and aliquoted into a plate for storage. During the course of preparation for an assay, the primary storage plate is automatically transferred from a storage incubator where it is maintained in a favorable environment to a liquid transfer module. A portion of the siRNA from each well is transferred to a destination plate from which the siRNA will be subsequently transferred to the plate or plates in which the assay is constructed. The primary storage plate is then returned to the incubator while the daughter storage plate is transferred to a subsequent dispensing module, such as a subnanoliter dispenser, where the siRNA is allocated to the wells of an assay plate. The database keeps track of the location of the primary source plate on its journey between the incubator and dispenser by recording barcode or other plate identifier information dynamically as the plate is conveyed into each module, which contains a barcode reader or other mechanism for identifying the plate. The database also records the amount of siRNA sample withdrawn from each well in the primary storage plate to keep track of the amount of the reagent that is maintained in storage and available for assays. In addition, the database keeps track of the dynamic location of the daughter source plate, containing the working dilution of the siRNA used in the assay. As this plate is effectively temporary, because the siRNA in it will be consumed in the assay, its records may be temporary.

Other databases in the first tier may be allocated to tracking the biosensor cell lines, chemical compound libraries that may be used to screen for action on the pathways probed by siRNA, and other entities that are useful for the design and construction of assays. Chemical compound library databases are isomorphic with siRNA databases. With respect to the biosensor cell lines, the information maintained in the database needed for assay design and construction is more specific to the nature of cell culture. For example, the database may contain records noting the date on which the biosensor cell line was originally constructed and links to assay data verifying the success of the various transformations or transfections needed for its construction as well as the pathway or pathways found to be monitored (e.g., an IFN-γ responsive pathway). It may also contain detailed data regarding which vectors, plasmids, viruses or other recombinant agents were used for its construction or its pathway activity readout mechanism (e.g., Green Fluorescent Protein or β-lactamase). Thus, the biosensor database may provide data to assay construction regarding the reagent or reagents needed to activate the biosensor pathway or the experimental conditions needed to measure the assay readout, such as the bandpass filters required in the assay readout detector. In addition, the biosensor cell line database may contain records noting the culture and propagation history of each cell line, such as amounts and locations in long-term cold storage, when the cell line was expanded for use in the assay and the cell density, as well as details needed for the assay such as special cell culture medium formulations needed to obtain stable growth or maintenance of the cells. Thus the first tier of information in compound management contains the location and amounts of reagents needed to construct an assay.

The second tier of information integrates the data regarding reagents available to the assay to control the construction and performance of the assay. This tier is built around the usage of the wells in the high-density multiwell assay plate or plates used to perform the assay. At this level, the user specifies the reagents and their amounts that will be added to each well in the plate or plates, their sequence of addition, the duration and location of incubation steps needed as the assay is built. For example, the user may specify a particular daughter source plate of siRNA generated at the first, reagent dilution level, and map the different siRNA sequences to the different grids specified on the assay plate or plates by allocating the specific well locations in the grid to contain siRNA. To produce dilutions of an siRNA, either different amounts of siRNA from the daughter source plate may be dispensed to those wells receiving the dilution, or the same amount may be dispensed to each well in the dilution series and then different amounts of diluent such as transfection medium may be specified for addition to each well. The user will then map the subsequent reagents needed to perform the assay to each grid, for example, designing control wells containing transfection reagent but no siRNA or other control wells, such as those lacking the pathway activator of the biosensor cell line. For reagents contained in plates, the plate identifiers are specified to enable the control system to determine their locations and to stage them at the appropriate locations in stacks, incubator hotels, or other locations. For reagents maintained in the supply bottles of the pressure-driven solenoid dispensers, the module identifier is needed to ensure delivery of those reagents to the assay wells. The information in the well usage map is conveyed by the control system to each dispensing module so that the correct reagents in their correct amounts are added to each well. The control system used in this second tier ensures the correct scheduling of the correct plates to the different modules at the needed times for successful assay construction and readout.

The second tier of information also includes analysis of the assay data into the outcome of each assay experiment—the action of the siRNA on the pathway probed by the biosensor cell line. This involves the processing of the signals recorded from each sample well by the assay signal readout instrumentation in an assay well grid into data that indicates the effect of knocking out each particular target on the pathway monitored in the biosensor cell line. For example, the instrumentation control well signals are subtracted from each well's signal to eliminate background signal of the detector, the multiwell plate material, and undeveloped assay signal reagents. In addition, the signals from wells containing biosensor cells untreated with siRNA and unstimulated with the pathway activation reagent are compared with the signals arising from activated, siRNA-untreated cells to establish the dynamic range of the assay. Biological background effects on the biosensor cell line arising from the transfection reagent or nonspecific action of small RNA are corrected by subtracting the signals arising in those wells from the signals of wells in which cells were treated with the siRNA. Finally, the action of the siRNA on the pathway probed by the biosensor cell line is determined by comparing the difference in signals between the activated and unstimulated cells transfected with siRNA to the dynamic range established with untransfected cells. In addition, replication of each condition enables comparisons to determine whether experimental errors arose in some wells, such as failures of dispensing, and those wells may be eliminated from analysis.

The third tier of information enables correlation of assay data and the gene products knocked out by siRNA. This correlation enables interpretation of the role of a gene product in a biochemical pathway or network. For each siRNA generated and employed in assays, the results of every assay performed are tabulated together with the gene product for which the siRNA was targeted. This allows an analysis to determine which biosensor cell lines exhibited an effect by the siRNA. On the basis of the pathway for which each biosensor cell line was designed to monitor, this analysis enables conclusions to be drawn regarding the participation of the targeted gene product in the pathway. In addition, for each biosensor cell line, the assay results obtained for each siRNA tested on the cell line can be compared to establish gene products that exert a role in the monitored pathway. This enables prediction of new targets in a pathway and may uncover both roles for gene products previously unsuspected to play much of a role in the pathway, the strengths of each pathway member, and the existence of gene products that provide links to other pathways that may bypass the particular pathway probed in the biosensor cell line.

Each siRNA is designed to knock out a particular gene product and this design is made on the basis of its complementarity to a predicted or known messenger RNA sequence. Multiple siRNA reagents may be designed for a particular message, and these reagents may vary in efficacy. Moreover, information may or may not exist already about the gene product of interest, such as its established roles in well-studied pathways. Gene sequences may be identified on the basis of transcription activation and termination elements present in chromosomal DNA sequences and the presence of identified introns, such that no actual functional information is known. At the final tier of information, the functions of the gene product of interest and its involvement in biochemical networks are discerned. Thus, compound management provides the main analytical engine for assay design and performance as well as integration of the resulting assay data into functional information about the gene products probed by using siRNA.

EXAMPLE 1

Automated Modular Components of an siRNA Screening Laboratory

The following example depicts a typical arrangement of automated high-throughput biology laboratory modules useful for siRNA screening in high-density multiwell plates and describes the functions of each module. The laboratory includes modules for the storage and incubation of plates, for dispensing liquids to the plates to construct assay samples, and for reading the signals generated by the assay samples in the plates.

The automated high-throughput biology laboratory is arranged around a rotary robotic arm located on a linear transport stage or track. The arm is used to transport plates between the different modules of the laboratory. A variety of arms are useful for plate transport, including the CataLyst5 track system (Thermo CRS) and the rotary articulating arms available from Mitubishi (e.g., MELFA RV2AJ). A dynamic plate gripper is located at the active end of the arm. The plate gripper is used to secure the plate to the arm during transport such that the plate is maintained in a horizontal position to avoid spilling of the contents. The articulation of the arm, the action of the plate gripper, and the translocation of the arm along the track are under command of a plate scheduling system that coordinates plate presentation to and reception from the arm by the different modules. To move a plate between two modules, the controller for the module containing the source plate actuates its plate handling device, which results in the selection of the requested plate and placement on a caddy or nest that moves the plate to a plate access point. The plate-handling device of the module may contain a device that removes the lid from the plate, or delidding may be performed by the robotic arm prior to removing the plate from the module. The arm is then articulated so that the open plate gripper may be positioned around the presented source plate. The gripper then is actuated by the scheduler to clamp the plate and remove it from the presentation caddy. The position of the arm when it grips the plate is specified so that the contact points of the gripper avoid the caddy and only contact the portions of the plate flange that do not rest on the caddy. In addition, the action of the plate gripping mechanism of the presentation caddy is coordinated with actuation of the plate gripper such that the plate is released and held free in the caddy prior to the plate gripping action of the arm. The plate is gripped by the arm and lifted free from the caddy. The arm then articulates to move the plate away from the source module and is translocated down the track to the destination module. The controller of the destination module then actuates presentation of its plate-handling caddy to the robotic arm. The arm articulates to lower the gripped plate into the destination caddy. When the plate contacts the caddy, the plate gripping mechanism of the caddy is actuated to grip the plate, and the gripper on the arm is actuated to release the plate. Coordination of handoff between the arm and the modules ensures that plate conveyance between modules can be successfully performed without manual intervention.

Plates may be stored and maintained under precise environmental conditions in incubator module(s) located along the track. The plates may be used for storage of assay reagents including cells, incubation and growth media, siRNA, or other reagents needed for the construction and performance of siRNA screening assays. In one embodiment of the invention, at least two incubators are used in which the environmental conditions such as temperature, humidity, atmospheric $CO_2$, or other conditions may be independently controlled. One incubator is used to maintain the individual reagents used to construct the assays. The other incubator is used to house the assay samples during the incubation steps that may be necessary as the assays are under construction and the constructed assays during the incubation period needed for the development of the assay signal. This ensures that contamination of assay construction reagents is minimized by the presence of completed assay samples.

Each incubator maintains the multiwell plates in repositories such as stackers or hotels. In the case of stackers, locating a plate requires maintenance of stacker loading information, such as the number of plates added to or removed from the stacker after the plate of interest was inserted. In the case of hotels, each plate is stored in a separate, identifiable location. The incubators provide the means for identifying each plate as it is inserted into and removed from the incubator such as a barcode reader for barcode information stamped on each plate. In addition, the incubator is capable of storing each identified plate at an identified location, so that each plate can be retrieved individually when requested. A variety of incubators with plate-handling capabilities are commercially available such as those made by Heraeus Instruments (e.g., Cytomat 6001). The incubators are fitted with automated plate caddies that are capable of receiving a plate from the robotic arm, or presenting a plate from the incubator to the arm, and transferring the plate to or from the internal plate transport system of the incubator. The plate caddies when moved to the external plate presentation or acceptance position are aligned with plate gripper of the-arm.

Fluid transfer for the purpose of constructing assays in multiwell assay plates is performed by 2 different modules located along the track. Each module is a station with integrated functionality including plate handling, capable of receiving plates from the robotic arm, queuing the plates for dispensing, dispensing to every well on each plate, and then presenting the plates to the arm for removal from the module. One module handles the dispensing of liquids by means of droplets less than 10 nl in volume (termed subnanoliter dispensing), while the other module provides dispensing of larger volumes between 10 nl and 1 µl (termed submicroliter dispensing).

Subnanoliter dispensing is performed with acoustic excitation by using an HTS-01 (EDC Biosciences), a Multiple Piezo Dispenser system (MPD, Aurora Discovery, Inc.), or other means capable of producing liquid drops in this volume range. Drop-on-demand dispensing allows the needed volume of reagent to be delivered accurately and precisely to each well on a multiwell plate that requires the reagent according to the well usage plan created for an assay. Individual reagents may be delivered to each well of the destination plate. In the case of the EDC HTS-01, a source plate of the same well density as the destination is filled such that each source well contains a single reagent mapped such the short dimension of the wells on the plate (the columns) are filled in reverse order to the order desired in the destination plate. The destination plate is inverted and aligned over the source plate, and the assembly is passed over the acoustic transducer such that the reagent in each source well is ejected up toward the corresponding destination well. With the MPD or other piezo dispensing system, the microcapillary dispensers are first lowered into the wells of a source plate for aspiration of each reagent into a separate microcapillary. Then the destination plate is moved under the dispenser head and the reagents are dispensed to the wells. The dispense controller of the module ensures that reagent is dispensed only to the wells of the plate designated in the well usage map.

Subnanoliter dispensing is useful for dispensing small volumes of relatively concentrated reagents to microliter-volume assay samples, such as the siRNA used to transfect a cell line. The typical concentration of siRNA used to transfect a sample of cells is 50 nM, or about 0.4 ng per µl of single-stranded 20-ribonucleotide length antisense RNA. This concentration of siRNA in the sample is easily obtained by dispensing to a 1 µl-volume assay sample a 500 pL aqueous drop of siRNA at a concentration of 0.8 mg/ml, which is an easily maintained concentrate of siRNA.

Submicroliter dispensing is performed by an integrated station such as the Flying Reagent Dispensing (FRD) robot (Aurora Discovery, Inc.). The FRD contains integrated plate capabilities and utilizes four solenoid-metered hydrostatic pressure-driven dispensers for the capability of delivering up to 4 different reagents to any or all wells of a high-density multiwell plate (e.g., 1536, 3456, or greater number of wells per plate). The plate is scanned under the fixed dispensing head and the solenoid valves are opened for the period of time needed to eject the prescribed volume as each well passes under each dispenser. Submicroliter dispensing is used to construct assay samples by the addition of concentrated, disaggregated cells, growth or other media, assay reagents such as fluorescent dyes used to develop the assay signal, reagents needed to facilitate cell uptake or activation of assay signal development reagents, or activators of signaling pathways for the initiation of biosensor cell assays.

Readout of the signal produced by the assay is performed using a modular signal detection station. This station also has integrated plate-handling capabilities for both acceptance and handoff of plates to the robotic arm as well as internal plate positioning capabilities in the reading apparatus. A commercially available station with these capabilities and also able to be integrated with the external track is the Topology-compensated Plate Reader (tcPR, Aurora Discovery, Inc.). In this device, the high-density multiwell plate is scanned over an optical head specialized for delivery of excitation light to fluorescence assays and measurement of the intensities of the resulting emitted fluorescence in multiple wavebands so that a variety of spectrometric modalities can be used as the basis for the assay signal. These modalities include multiple fluorophores, resonance energy transfer as a proximity measurement of multiple fluorophores, luminescence, and time-resolved fluorescence. The plate is moved in a continuous pattern so that each well in a high-density multiwell plate is illuminated and read from beneath by the optical head, e.g., 120 s for 3456 wells with a >50 msec excite and read time for each well. In addition, the module may be fitted with liquid-dispensing capabilities, such as the solenoid-metered pressure-driven system of the FRD. This enables kinetic measurements to be performed by using the dispenser to add an activator of the signal transduction pathway of the biosensor cell line to each well at a prescribed time relative to illumination and reading of the well with the optical head.

EXAMPLE 2

A Biosensor Cell Line for siRNA Screening

The biosensor cell line is a cell line that enables the activity of a specific signal transduction pathway to be monitored by measuring fluorescence of an exogenously added fluorescent reagent. The cell line is useful for siRNA screening by knocking out different gene products comprising the signal transduction pathway. The biosensor cell is constructed by transfection with different expression vectors that encode reporter genes, membrane receptors for pathway activators, and components of the signal transduction mechanism. In this example, the reporter gene encodes βlactamase, which produces a change in the fluorescence of the signaling reagent CCF2. CCF2 is a fluorescence energy transfer reagent consisting of a coumarin group linked to a fluorescein group by a cephalosporin moiety. In the absence of β-lactamase expression, excitation of the coumarin with light in the wavelength range of 390 to 430 nm results in non-photonic transfer of excitation from the coumarin to the covalently linked fluorescein such that the fluorescence of the coumarin is quenched but the fluorescein is excited and emits light in the wavelength range of 520 to 570 nm. When β-lactamase is expressed by activation of the reporter gene, the enzyme cleaves the cephalosporin moiety resulting in liberation of the fluorescein and coumarin groups and the elimination of energy transfer. Excitation of the coumarin then results in emission of light in the range of 440 to 490 nm with little concomitant excitation of the fluorescein. Thus, in the presence of expressed β-lactamase, the light emission spectrum of an assay shifts from ~530 nm to 460 nm. Although CCF2 is cell membrane impermeant, the acetoxylated molecule is permeant and relatively non-fluorescent, so that cells may be loaded with acetoxy-CCF2 which is activated by intracellular esterases to fluorescent CCF2. Net uptake is promoted by inhibition of anion transporters with blockers such as probenecid.

The biosensor cell line in this example was constructed from Jurkat cells. The cells were constructed to stably express an M1 muscarinic receptor and to contain a plasmid encoding β-lactamase linked to a NFAT promoter element. The cells used for this example were prepared transfecting wild-type Jurkat cells with plasmid 3XNFAT-blax-zeo, which contains 3 upstream NFAT expression control regions from the region encoding β-lactamase and then with pcDNA3-M1 as described by Coassin et al, 2003. The wild-type cells transfected with 3XNFAT-blax-zeo were selected by culture in serum-supplemented RPMI medium containing zeocin, and selected for expression of β-lactamase under NFAT transcription control by fluorescence-activated cell sorting in the presence of CCF2 and thapsigargin. The sequence encoding the M1 receptor in the second plasmid was under expression control by an IFN control element, as described.

The biosensor cell line provides a signal transduction pathway or set of signal transduction pathways whose activity or activities can be measured by the fluorescence changes in CCF2 due to expression of the reporter gene product, β-lactamase. Activation of the expressed M1 receptor by a muscarinic agonist such as acetylcholine or carbachol results in activation of phospholipase C mediated by a heterotrimeric G protein. Activated phospholipase C cleaves phosphatidylinositol in the plasmalemma to diacylglycerol and inositol triphosphate. The diacylglycerol activates protein kinase C, which initiates other specific intracellular signaling pathways. The inositol triphosphate diffuses intracellularly and opens ITP-sensitive $Ca^{2+}$ channels in the endoplasmic reticulum, resulting in an elevation of the intracellular concentration of free $Ca^{2+}$. This free $Ca^{2+}$ activates the calcium-dependent phosphatase calcineurin, which dephosphorylates the soluble phosphorylated NFAT promoter binding protein enabling it to bind to the NFAT expression control element and activate gene expression. Thus, the biosensor cell line provides numerous targets in the heterotrimeric G-protein coupled phospholipase C activated signal transduction pathway for interference by siRNA.

It is possible to construct a wide variety of biosensor cell lines using reporter gene products such as β-lactamase, luciferase, green fluorescent proteins, and others. For example, signal transduction pathways converging on the cyclic nucleotide response element CREB can be created by linking CREB sequences upstream of the reporter gene. In addition, novel lines can be created by use of transposition elements flanking the reporter gene, such that the transfection vector is able to insert the reporter in the genome (GenomeScreen, Invitrogen, Carlsbad, Calif.). This insertion may be either at random or in a targeted manner using other sequences flanking the reporter gene that enable recombination at the homologous set of sequences in the genome. An application of random insertion could be to discover insertion sites responsive to stimulation of the cell with chemokines such as IFN-γ. It is known that a potential drawback to the therapeutic usage of siRNA in humans is the stimulation of an interferon response in cells. In this interferon response, generated primarily by siRNA produced by phage RNA polymerases rather than by chemically synthesized siRNA, interferon expression is induced as well as expression of the some 100 or more genes that respond to activation of the membrane interferon receptor. Interferon-responsive biosensors obtained by the random insertion of reporter genes and screened for interferon-induced activation of the reporters may provide opportunities to measure such inflammatory response effects of siRNA and provide experimental controls in siRNA screening experiments.

EXAMPLE 3

Real-time Gene Expression Knock-out by siRNA

In this example, the carbachol-activatable Jurkat biosensor cell line is used to examine the knocking out of an intracellular calcineurin. The siRNA sequence is designed by the use of SMARTselection and SMARTpool technologies and synthesized (Dharmacon RNA Technologies, Boulder, Colo.). SMARTselection provides rational design of the sequence to minimize certain undesirable features of 21- and 22-base oligomers, such as foldback hybridization, low or high duplex melting temperature, and other features that interfere with message specificity. SMARTpool provides for the generation of up to 6 separate siRNA sequences designed to hit the same target message. Combinations of siRNA sequences targeted to the same message have been shown to result in greater knock down of target message than a single siRNA sequence. A screen may be designed to test each sequence singly and in different combinations to isolate the most potent mixture. For transfection, the individual sequences are mixed with the Dharmacon TKO custom transfection reagent to yield a concentration of 4 μg siRNA/μl and 1 μl is added to each well of a high-density multiwell plate using an FRD. The assay plate is prepared by adding 0.5 μl of $2\times10^6$/ml biosensor cells (1000 cells) in growth medium to each well of a high-density multiwell plate. The plate is incubated for 24 hr at 37° C. to allow the cells to multiply and adhere to the well bottoms.

The cells are then transfected by addition of the siRNA in transfection reagent. The source plate containing the siRNA-transfection reagent complexes are passed to the MPD where 0.5 μl of each siRNA sample is aspirated into each piezo dispenser. The source, plate is removed and then 1 nl of siRNA is dispensed to each well in the assay plate designated to receive siRNA in the experimental design. The cells are returned to the incubator for a 5 hr incubation to enable the siRNA to enter the cells and to begin inducing degradation of the target message. The assay plate is then sent to the FRD where the assay signal development reagents are added in a 0.5 μl aliquot consisting of 2 μg/ml CCF2-AM and 10 mM probenecid in growth medium. The assay plate is returned to the incubator for 2 hr to allow the CCF2-AM to permeate the cells and to be deacetoxylated by intracellular esterases to produce the fluorescent substrate for β-lactamase.

To run the assay, the assay plate is sent to the FRD where the pathway activator carbachol concentrate is dispensed to designated wells to achieve a final concentration of 50 μM carbachol. The wells in the assay plate dosed with carbachol and the appropriate control wells are then read by recording the fluorescence light intensity at 460 nm and 530 nm on excitation with 400 nm light. Over a time course of 12 hours, the plate is repeatedly passed between the carbachol dispensing FRD and the plate reader so that a sequence of wells is successively dosed and read at fixed times following activation of the biosensor pathway. By varying the time post-transfection with siRNA and the initiation of the M1 receptor-dependent pathway, the kinetics of calcineurin message synthesis is determined. By varying the time between the addition of carbachol and the reading of the β-lactamase-dependent ratio of 460 nm and 530 nm light emission at each fixed time point following transfection of the biosensor cell line with siRNA, the effect of calcineurin depletion on the kinetics of the M1 receptor-dependent signal transduction pathway is determined.

FIG. 5a shows a dispensing table for a siRNA knockdown experiment indicating the reagents dispensed to each control or experimental condition. The "no siRNA stimulated" and "no siRNA unstimulated" conditions serve as controls for the transfection reagent in the absence of siRNA and are used to establish the dynamic range of the assay in the cells.

FIG. 5b shows a map of conditions to wells in a single 6×6 well grid on a 1536 or 3456 plate. Each condition is replicated 4 times and distributed across the edge and non-edge wells of the grid to control for a well-position effect. This example shows that the automated laboratory is capable of monitoring the effects of siRNA on gene expression kinetics.

The automated high-throughput biology laboratory 100 disclosed represents a major change in the way screening may be done. Instead of transferring the assay to a centralized facility, scientists can run screens themselves. Screening becomes an experiment as one scientist can easily screen 100,000 compounds in a day. Because the system is small, it can fit into a laboratory where scientists have access to it for assay development as well as screening. Assays can be developed and validated on the same system where the screen will be run. Moreover, having access to the compound library gives the scientist the ability to follow up on interesting compounds immediately instead of waiting for a centralized facility to process a compound request. The scientist also has the freedom to decide how to run the experiment by choosing number of replicates, concentration of compounds, etc.

Another advantage of storing compounds in high-density microplates is the small volume of expensive compound required to make a usable source plate. This allows compound libraries to be replaced often to ensure compound stability. The nanoliter dispenser can dispense from a 3456-well source plate whose volume is between 0.5 and 2 µL. This means that with 2 µL of compound, it can deliver 10 nL to 150 separate target locations, wasting only 0.5 µL. By contrast, most aspirate/dispense devices (including inkjet-type nanoliter dispensers) must aspirate at least 1 µL every time they access a new compound. These types of pipetters require at least 5 µL of volume in the source well and can only access liquid in 96- or 384-well plates. A typical low-density source plate would be filled initially with about 50 µL so that it could be accessed at most 45 times, wasting 5 µL.

Because it is relatively painless to make a copy of a compound library in high-density microplates, multiple copies can be distributed throughout an organization. Each lab can have its own fully-integrated screening system complete with a set of compounds.

The automated high-throughput biology laboratory 100 can perform wet addition, adding compounds to assay microplates that have already been filled with reagent. This is useful because some cells perform better after adhering to a surface. These cells must be added to the assay plate and allowed to sit overnight before compounds can be added. No other high-density screening system can do this.

Additional details of a high-density microplate may be found in U.S. Patent Application Publication No. 2005/0048575, published Mar. 3, 2005, titled, MULTI-WELL PLATE PROVIDING A HIGH-DENSITY STORAGE AND ASSAY PLATFORM, based upon U.S. Provisional Application No. 60/466,998, filed Apr. 30, 2003, titled, DUAL-USE HIGH-DENSITY MICROPLATE, and U.S. Provisional Application No. 60/493,415, filed Aug. 6, 2003, titled, MULTI-WELL PLATE PROVIDING A HIGH-DENSITY STORAGE AND ASSAY PLATFORM, the contents of which are incorporated by reference in their entirety.

Additional details of dispensing liquids may be found in U.S. Patent Application Publication No. 2005/0006417, published Jan. 13, 2005, titled, METHOD AND SYSTEM FOR PRECISE DISPENSATION OF A LIQUID, based upon U.S. Provisional Application No. 60/467,062, filed Apr. 30, 2003, titled, FLUID MICRODISPENSER DISCHARGE ORIFICE, the contents of which are incorporated by reference in their entirety.

While an exemplary drawings and specific embodiments of the present invention have been described and illustrated, it is to be understood that that the scope of the present invention is not to be limited to the particular embodiments discussed. Thus, the embodiments shall be regarded as illustrative rather than restrictive, and it should be understood that variations may be made in those embodiments by workers skilled in the arts without departing from the scope of the present invention as set forth in the appended claims and structural and functional equivalents thereof.

In addition, in methods that may be performed according to preferred embodiments herein and that may have been described above and in the claims below, the operations have been described in selected typographical sequences. However, the sequences have been selected and so ordered for typographical convenience and are not intended to imply any particular order for performing the operations.

What is claimed is:

1. An automated high-throughput biology laboratory, comprising:

a plurality of removable modules having module controllers, the plurality of removable modules being arranged in a layout and each module capable of being added or removed from the layout, at least one module being a dispenser module capable of dispensing one or more liquids into one or more wells of a high-density microplate and at least one module being an assay signal detection module capable of detection and measurement of physical signals of an assay in the wells of the high-density microplate;

one or more plate transports located near a center of the layout capable of transporting the high-density microplates between the plurality of removable modules within the layout; and a system controller in communication with the transports and the module controllers in the layout, the system controller having one or more stored codes configured to communicate with the module controllers to operate any of the plurality of removable modules in the layout and the system controller being capable of polling the status of the module controllers to determine when the removable modules are inserted into or removed from the layout and adjusting the stored codes needed in response to the insertion or removal of a removable module from the layout.

2. The biology laboratory of claim 1, wherein each of the modules includes a plate access port accessible by the plate transport.

3. The biology laboratory of claim 1, wherein the dispenser modules includes at least one microliter dispenser module and at least one nanoliter dispenser module.

4. The biology laboratory of claim 1, wherein the signal detection module is a spectrometric reader module capable of reading a fluorescence signal.

5. The biology laboratory of claim 1, wherein at least one module further comprises one or more plate carousel modules.

6. The biology laboratory of claim 1, wherein at least one module further comprises one or more incubator modules.

7. The biology laboratory of claim 1, wherein at least one module further comprises one or more centrifuge modules.

8. The biology laboratory of claim 1, wherein at least one module further comprises one or more kinetic assay modules.

9. The biology laboratory of claim 1, wherein the system controller is programmable.

10. The biology laboratory of claim 1, wherein the system controller is capable of controlling the movement of the high-density microplates.

11. The biology laboratory of claim 1, wherein the system controller is capable of topographical mapping the high-density microplates.

12. The biology laboratory of claim 1, wherein the dispenser module includes an acoustic dispenser.

13. The biology laboratory of claim 1, wherein the plate transport includes a plate gripper located at the end of an articulated arm.

14. The biology laboratory of claim 1, further comprising a mechanism in communication with the system controller for identifying the high-density microplates.

15. The biology laboratory of claim 14, wherein the mechanism is one or more barcode readers.

16. A method for screening a compound using an automated high-throughput biology laboratory, comprising:
   providing a biology laboratory comprising:
      a plurality of removable modules having module controllers, the plurality of removable modules being arranged in a layout and each module capable of being added or removed from the layout, at least one module being a dispenser module capable of dispensing one or more liquids into one or more wells of a high-density microplate and at least one module being an assay signal detection module capable of detection and measurement of physical signals of an assay in the wells of the high-density microplate;
      one or more plate transports located near a center of the layout capable of transporting the high-density microplates between the plurality of removable modules within the layout; and
      a system controller in communication with the transports and the module controllers in the layout, the system controller having one or more stored codes configured to communicate with the module controllers to operate any of the plurality of removable modules in the layout and the system controller being capable of polling the status of the module controllers to determine when the removable modules are inserted into or removed from the layout and adjusting the stored codes needed in response to the insertion or removal of a removable module from the layout;
   providing one or more high-density microplates having a plurality of wells;
   selectively dispensing one or more reagents into one or more wells of the high-density microplates with a microliter dispenser module;
   selectively dispensing droplets of the compound directly from a storage plate into one or more wells of the high-density microplates with a nanoliter dispenser module; and
   reading the physical signals of an assay in the wells of the high-density microplate with the signal detection module.

17. The method of claim 16, further comprising inserting or extracting one or more high-density microplates from an incubator module in the layout.

18. The method of claim 16, further comprising inserting or extracting one or more high-density microplates from a plate carousel module in the layout.

19. The method of claim 16, further comprising inserting or extracting one or more high-density microplates from a centrifuge module in the layout.

20. The method of claim 16, further comprising inserting or extracting one or more high-density microplates from a kinetic assay module in the layout.

21. The method of claim 16, further comprising determining when modules are inserted into or removed from the layout with the system controller.

22. The method of claim 16, further comprising programming the system controller to control the movement of the high-density microplates.

23. The method of claim 16, further comprising mapping the high-density microplates with the system controller to provide a topographical map.

24. The method of claim 16, further comprising tracking the high-density microplates using one or more barcode readers in communication with the system controller.

25. An automated high-throughput biology laboratory, comprising:
   a plurality of removable modules having module controllers, the plurality of removable modules being arranged in a layout and each removable modules capable of being added or removed from the layout, the plurality of removable modules including:
      at least one microliter dispenser capable of dispensing liquids into one or more wells of a high-density microplate;
      at least one nanoliter dispenser capable of dispensing liquids into one or more wells of a high-density microplate; and
      at least one plate reader capable of detection and measurement of physical signals of an assay in the wells of the high-density microplate;
   one or more plate transports capable of transporting high-density microplates between the plurality of removable modules; and
   a system controller in communication with the transports and the module controllers in the layout, the system controller having one or more stored codes configured to communicate with the module controllers to operate any of the plurality of removable modules in the layout and the system controller being capable of polling the status of the module controllers to determine when the removable modules are inserted into or removed from the layout and adjusting the stored codes needed in response to the insertion or removal of a removable module from the layout.

26. The biology laboratory of claim 25, wherein each of the modules includes a plate access port accessible by the plate transport.

27. The biology laboratory of claim 25, wherein the plurality of removable modules further includes one or more plate carousels.

28. The biology laboratory of claim 27, wherein one or more plate carousels stores library of compound microplates.

29. The biology laboratory of claim 27, wherein one or more plate carousels stores library of assay microplates.

30. The biology laboratory of claim 25, wherein the plurality of removable modules further includes one or more incubators.

31. The biology laboratory of claim 25, wherein the plurality of removable modules further includes one or more centrifuge modules.

32. The biology laboratory of claim 25, wherein the plurality of removable modules further includes one or more kinetic assay modules.

33. The biology laboratory of claim 25, wherein the plate reader is a spectrometric reader capable of reading a fluorescence signal.

34. The biology laboratory of claim 25, wherein the system controller is programmable.

35. The biology laboratory of claim 25, wherein the system controller is capable of controlling the movement of the high-density microplates.

36. The biology laboratory of claim 25, wherein the system controller is capable of topographical mapping the high-density microplates.

37. The biology laboratory of claim 25, wherein the plate transport includes a plate gripper located at the end of an articulated arm.

38. The biology laboratory of claim 25, further comprising a mechanism in communication with the system controller for identifying the high-density microplates.

39. The biology laboratory of claim 38, wherein the mechanism is one or more barcode readers.

* * * * *